(12) United States Patent
Olson et al.

(10) Patent No.: US 7,447,643 B1
(45) Date of Patent: Nov. 4, 2008

(54) SYSTEMS AND METHODS FOR COMMUNICATING BETWEEN A DECISION-SUPPORT SYSTEM AND ONE OR MORE MOBILE INFORMATION DEVICES

(75) Inventors: Jonathan B. Olson, Salt Lake City, UT (US); Mark H. Skolnick, Salt Lake City, UT (US); Stanley L. Pestotnik, Sandy, UT (US); William F. Harty, III, Salt Lake City, UT (US); Richard J. Boekweg, Tooele, UT (US); Bo Lu, Salt Lake City, UT (US); Merle A. Sande, Salt Lake City, UT (US)

(73) Assignee: Theradoc.com, Inc., Salt Lake City, UT (US)

( * ) Notice: Subject to any disclaimer, the term of this patent is extended or adjusted under 35 U.S.C. 154(b) by 919 days.

(21) Appl. No.: 09/666,445

(22) Filed: Sep. 21, 2000

(51) Int. Cl.
*G06Q 10/00* (2006.01)

(52) U.S. Cl. .............................. 705/2; 434/236; 706/46

(58) Field of Classification Search ................ 705/2–3; 600/300, 301; 604/131; 340/5, 61; 434/236; 706/46

See application file for complete search history.

(56) References Cited

U.S. PATENT DOCUMENTS

| | | | |
|---|---|---|---|
| 3,697,693 A | 10/1972 | Deschenes et al. | |
| 4,290,114 A | 9/1981 | Sinay | 364/900 |
| 4,491,725 A | 1/1985 | Pritchard | |
| 4,648,037 A | 3/1987 | Valentino | |
| 4,797,543 A | 1/1989 | Watanabe | |
| 4,817,018 A | 3/1989 | Cree et al. | |
| 4,819,191 A | 4/1989 | Scully et al. | |
| 4,839,822 A | 6/1989 | Dormond et al. | 364/513 S |
| 4,858,121 A | 8/1989 | Barber et al. | |
| 4,868,763 A | 9/1989 | Masui et al. | 364/513 |
| 4,916,611 A | 4/1990 | Doyle, Jr. et al. | |
| 5,018,067 A | 5/1991 | Mohlenbrock et al. | 364/413.02 |

(Continued)

OTHER PUBLICATIONS

Lifechart.com Takes Next Step to Monitoring Health Online: First E-Health Company of Its Kind to Expand Services With Wireless Applications by PR Newswire, New York: Apr. 12, 2001, p. 1).*

(Continued)

*Primary Examiner*—Vanel Frenel
(74) *Attorney, Agent, or Firm*—Workman Nydegger

(57) ABSTRACT

A decision-support system for providing a clinician with real-time patient data specific to each patient that the clinician is to examine in a defined time period. The system including a decision-support module that is configured to generate decision-supported patient data that is specific to each patient that a clinician is to examine in a defined time period. The decision-support module including an inference engine that communicates with a knowledge module and a patient module to generate the decision-supported patient data. In real-time communication with the decision-support module is a user module that is adapted to present the decision-supported patient data in real-time to the clinician in a configuration that assists the clinician in treating each patient. The user module further allowing the clinician to changes elements of the decision-supported patient data and receive new recommendations and medical care suggestions in real-time from the decision-support module.

33 Claims, 4 Drawing Sheets

U.S. PATENT DOCUMENTS

| | | | |
|---|---|---|---|
| 5,050,077 A | 9/1991 | Vincent | |
| 5,124,912 A | 6/1992 | Hotaling et al. | |
| 5,197,000 A | 3/1993 | Vincent | |
| 5,255,187 A | 10/1993 | Sorensen | 364/413.02 |
| 5,299,121 A | 3/1994 | Brill et al. | 364/413.01 |
| 5,301,105 A | 4/1994 | Cummings, Jr. | 364/401 |
| 5,342,922 A | 8/1994 | Marshall et al. | 530/329 |
| 5,343,869 A * | 9/1994 | Pross et al. | 600/301 |
| 5,355,444 A | 10/1994 | Chirico | 395/51 |
| 5,473,537 A | 12/1995 | Glazer et al. | 364/419.2 |
| 5,517,405 A * | 5/1996 | McAndrew et al. | 706/45 |
| 5,551,436 A | 9/1996 | Yago | 128/670 |
| 5,583,758 A | 12/1996 | McIlroy et al. | 395/202 |
| 5,594,638 A | 1/1997 | Iliff | 395/203 |
| 5,660,176 A | 8/1997 | Iliff | 128/630 |
| 5,672,154 A | 9/1997 | Sillén et al. | 604/50 |
| 5,694,950 A | 12/1997 | McMichael | 128/898 |
| 5,737,539 A | 4/1998 | Edelson et al. | 395/203 |
| 5,748,907 A | 5/1998 | Crane | |
| 5,764,923 A | 6/1998 | Tallman et al. | 395/203 |
| 5,772,585 A * | 6/1998 | Lavin et al. | 600/300 |
| 5,778,346 A | 7/1998 | Frid-Nielsen et al. | |
| 5,833,599 A | 11/1998 | Schrier et al. | 600/300 |
| 5,839,438 A | 11/1998 | Graettinger et al. | 600/300 |
| 5,845,255 A | 12/1998 | Mayaud | 705/3 |
| 5,848,395 A | 12/1998 | Edgar et al. | |
| 5,867,822 A | 2/1999 | Sankar | |
| 5,899,979 A | 5/1999 | Miller et al. | |
| 5,908,383 A | 6/1999 | Brynjestad | 600/300 |
| 5,911,132 A | 6/1999 | Sloane | 705/3 |
| 5,924,074 A | 7/1999 | Evans | 705/3 |
| 5,950,630 A | 9/1999 | Portwood et al. | 128/897 |
| 5,960,085 A * | 9/1999 | de la Huerga | 340/5.61 |
| 6,009,420 A | 12/1999 | Fagg, III et al. | 706/45 |
| 6,018,713 A | 1/2000 | Coli et al. | 705/2 |
| 6,029,138 A | 2/2000 | Khorasani et al. | 705/2 |
| 6,049,794 A | 4/2000 | Jacobs et al. | 706/45 |
| 6,081,786 A | 6/2000 | Barry et al. | 705/3 |
| 6,081,789 A | 6/2000 | Purcell | 705/3 |
| 6,149,585 A | 11/2000 | Gray | |
| 6,151,581 A | 11/2000 | Kraftson | |
| 6,177,940 B1 | 1/2001 | Bond et al. | |
| 6,188,988 B1 | 2/2001 | Barry et al. | 705/3 |
| 6,195,612 B1 | 2/2001 | Pack-Harris | |
| 6,234,964 B1 | 5/2001 | Iliff | 600/300 |
| 6,246,975 B1 | 6/2001 | Rivonelli et al. | 703/11 |
| 6,247,004 B1 | 6/2001 | Moukheibir | 706/46 |
| 6,272,481 B1 | 8/2001 | Lawrence et al. | 706/45 |
| 6,283,761 B1 * | 9/2001 | Joao | 434/236 |
| 6,317,719 B1 | 11/2001 | Schrier et al. | 705/2 |
| 6,345,260 B1 | 2/2002 | Cummings, Jr. et al. | |
| 6,442,432 B2 * | 8/2002 | Lee | 607/59 |
| 6,443,889 B1 | 9/2002 | Groth et al. | 600/300 |
| 6,482,156 B2 | 11/2002 | Iliff | 600/300 |
| 6,678,669 B2 | 1/2004 | Lapointe et al. | |
| 6,694,298 B1 * | 2/2004 | Teagarden et al. | 705/3 |
| 6,754,655 B1 * | 6/2004 | Segal | 707/6 |
| 6,804,656 B1 | 10/2004 | Rosenfeld | |
| 6,849,045 B2 * | 2/2005 | Iliff | 600/300 |
| 7,069,227 B1 | 6/2006 | Lintel, III et al. | |
| 2001/0050610 A1 | 12/2001 | Gelston | 340/5.53 |
| 2002/0002472 A1 | 1/2002 | Abraham-Fuchs | 705/3 |
| 2002/0002473 A1 | 1/2002 | Schrier et al. | 705/3 |
| 2002/0040282 A1 | 4/2002 | Bailey et al. | 702/188 |
| 2002/0080189 A1 | 6/2002 | Dvorak et al. | 345/810 |
| 2002/0083075 A1 | 6/2002 | Brummel et al. | 707/102 |
| 2002/0091687 A1 | 7/2002 | Eglington | 707/5 |
| 2002/0099273 A1 | 7/2002 | Bocionek et al. | 600/300 |
| 2002/0107824 A1 | 8/2002 | Ahmed | 706/46 |
| 2002/0116222 A1 | 8/2002 | Wurster | 705/2 |
| 2002/0143262 A1 | 10/2002 | Bardy | 600/508 |
| 2002/0178031 A1 | 11/2002 | Sorenson | 705/2 |
| 2004/0015132 A1 * | 1/2004 | Brown | 604/131 |
| 2004/0260666 A1 | 12/2004 | Pestotnik et al. | 706/46 |

OTHER PUBLICATIONS

Optimizing the task of menu selection for large controlled vocabularies by Poon, Alex Dai-Shun, Ph.D., Standford University, 1997, 134 pages; AAT 9714176).*

Integra LifeSciences and QuadraMed Corporation Announce Joint Agreement for New Clinical Information Systems By PR Newswire. New YORK: Mar. 18, 1998. p. 1).*

"Life chart .com Takes Next Step to monitoring Health Online: First E-Health company of Its Kind to Expand Services With Wireless Applications" by PR Newswire (New York: Apr. 12, 2000.p. 1).*

Evans et al., A Computer-assisted Management Program for Antibiotics and Other Antiinfective agents; *The New England Journal of Medicine*, 338:232-238 (Jan. 22, 1998).

Pestonik et al., Implementing Antibiotic Practice Guidelines Through Computer-Assisted Decision Support: Clinical and Financial Outcomes; *Annals of Internal Medicine*, vol. 124, No. 10, 884-890 (1996).

Evans et al., A Decision Support Tool for Antibiotic Therapy; *AMIA, Inc.*, 651-655 (Oct. 1995).

Evans et al., Improving Empiric Antibiotic Selection Using Computer Decision Support; *Arch Internal Medicine*, vol. 154, 878-884 (Apr. 25, 1994).

Evans et al., Development of an Automated Antibiotic Consultant; *Clinical Computing*, vol. 10, No. 1; 17-22 (1993).

Plaintiff Allcare's Claim Chart Amendments in Response to Stipulated Order Regarding Same, Jun. 27, 2000, 14 pgs.

Alpay, L., et al., "Model-Based Application: The Galen Structured Clinical User Interface," pp. 307-318.

Arkad, K., et al., "Medical Logic Module (MLM) representation of knowledge in a ventilator treatment advisory system," *International Journal of Clinical Monitoring and Computing*, 1991, pp. 43-48.

Armstrong, Carl W., "AHA Guide to Computerized Physician Order-Entry Systems," American Hospital Association, Nov. 2000, pp. 1-48.

Astion, Michael L., et al., "Application of Neural Networks to the Classification of Giant Cell Artertis," *Arthritis & Rheumatism*, vol. 37, No. 5, May 1994, pp. 760-770.

Astion, Michael L., et al., "Neural Networks as Expert Systems in Rheumatic Disease Diagnosis: Artificial Intelligence or Intelligent Artifice?" *The Journal of Rheumatology*, 1993, vol. 20, No. 9, pp. 1465-1468.

Austin, Tony et al., "A Prototype Computer Decision Support System for the Management of Asthma," *Journal of Medical Systems*, vol. 20, No. 1, 1996, pp. 45-55.

Aydin, Carolyn E., et al., "Transforming Information Use in Preventive Medicine: Learning to Balance Technology with the Art of Caring," pp. 563-567, available on information and belief at least as early as 1994.

Balas, E. Andrew et al., "Improving Preventive Care by Prompting Physicians," *Arch Intern Med*, vol. 160, Feb. 14, 2000, pp. 301-308.

Balas, E. Andrew et al., "The Clinical Value of Computerized Information Services—A Review of 98 Randomized Clinical Trials," *Arch Fam Med*, vol. 5, May 1996, pp. 271-278.

Bates, David W., "Using information technology to reduce rates of medication errors in hospitals," *BMJ*, vol. 320, Mar. 18, 2000, pp. 788-791.

Bates, David W., et al., "The Impact of Computerized Physician Order Entry on Medication Error Prevention," *Journal of the American Medical Informatics Association*, Jul./Aug. 1999, vol. 6, No. 4, pp. 313-321.

Berger, Jeffrey, "Roentgen: Radiation Therapy and Case-based Reasoning," pp. 171-177.

Bernstein, Robert M., "Prompting Physicians For Cost-Effective Test-Ordering in The Low Prevalence Conditions of Family Medicine," pp. 824-828, available on information and belief at least as early as 1994.

Bichindaritz, Isabelle, "A Case-Based Assistant for Clinical Psychiatry Expertise," pp. 673-677.

Brickley, R., et al., "Performance of a Neural Network Trained to Make Third-molar Treatment-planning Decisions," pp. 153-160, available on information and belief at least as early as 1994.

Burke, J.P., et al., "Computer-Assisted Prescribing and its Impact on Resistance," *Antibiotic therapy and control of antimicrobial resistnce in hospitals*, pp. 89-95, available on information and belief at least as early as 1999.

Burke, J.P., et al., "Antibiotic Use and Microbial Resistance in Intensive Care Units: Impact of Computer-Assisted Decision Support," *Journal of Chemotherapy*, vol. 11, No. 6, 1999, pp. 530-535.

Carenini, Giuseppe et al., "An Information-Based Bayesian Approach to History Taking," pp. 129-138.

Carson, E.R., et al., "Evaluating Intelligent Measurement Systems: A Study in Ventilator Management," *IEEE Engineering in Medicine & Biology Society 11th Annual International Conference*, pp. 1769-1770, available on information and belief at least as early as 1989.

Casanova, Andrea et al., "Reasoning with Cases in Clinical Problem Solving," pp. 1986-1990, available on information and belief at least as early as 1995.

Chambrin, Marie-Christine et al., "RESPAID: Computer Aided Decision Support for Respiratory Data in I.C.U.," *IEEE Engineering in Medicine & Biology Society 11th Annual International Conference*, pp. 1776-1777, available on information and belief at least as early as 1989.

Cheung, John Y., et al., "Detection of Abnormal Electrocardiograms Using a Neural Network Approach," *IEEE Engineering in Medicine & Biology Society 11th Annual International Conference*, pp. 2015-2016, available on information and belief at least as early as 1989.

Classen, David C., et al., "Description of a Computerized Adverse Drug Event Monitor Using a Hospital Information System," *Hospital Pharmacy*, vol. 27, Sep. 1992, pp. 774, 776-779, 783.

Darmoni, Stéfan J., et al., "Functional Evaluation of Seth: An Expert System in Clinical Toxicology," pp. 231-238, available on information and belief at least as early as 1994.

Davis, Randall, et al., "Retrospective on 'Production rules as a representation for a knowledge-based consultation program,'" *Artificial Intelligence 59* (1993), pp. 181-189.

DeJesus, Edmond X., "Achieving Expert Ease," *Healthcare Infromatics: Achieving Expert Ease*, Jan. 2000, pp. 1-10.

Do Amaral, M.B., et al., "A Psychiatric Diagnostic System Integrating Probabilistic and Categorical Reasoning," *Methods of Information in Medicine*, 1995, vol. 34, No. 3, pp. 232-243.

Dojat, Michel et al., "Evaluation of a Knowledge-based System Providing Ventilatory Management and Decision for Extubation," *American Journal of Respiratory and Critical Care Medicine*, vol. 153, 1996, pp. 997-1004.

Downs, Joseph et al., "A Prototype Neural Network Decision-Support Tool for the Early Diagnosis of Acute Myocardial Infarction," pp. 355-366.

Doyle, H.R., et al., "Building Clinical Classifiers Using Incomplete Observations—A Neural Network Ensemble for Hepatoma Detection in Patients with Cirrhosis," *Methods of Information in Medicine*, 1995, 6 pages.

Ebell, Mark H., "Artificial Neural Netowrks for Predicting Failure to Survive Following In-Hospital Cardiopulmonary Resuscitation," *The Journal of Family Practice*, vol. 36, No. 3, pp. 297-303, 1993.

Eccles, Martin et al., "Effect of computerised evidence based guidelines on management of asthma and angina in adults in primary care: cluster randomised controlled trial," *BMJ*, vol. 325, Oct. 26, 2002, pp. 1-7.

Evans, Carl D., et al., "A Case-Based Learning Approach to Grouping Cases with Multiple Malformations," *MD Computing*, 1995, vol. 12, No. 2, pp. 127-136.

Evans, R. Scott et al., "Improving Empiric Antibiotic Selection Using Computer Decision Support," *Archives of Internal Medicine*, vol. 154, Apr. 25, 1994, pp. 878-884.

Evans, R. Scott et al., "Reducing the Duration of Prophylactic Antibiotic Use Through Computer Monitoring of Surgical Patients," *DICP, The Annals of Pharmacotherapy*, Apr. 1990, vol. 24, pp. 351-354.

Evans, R. Scott et al., "Preventing Adverse Drug Events In Hospitalized Patients," *The Annals of Pharmacotherapy*, vol. 28, Apr. 1994, pp. 523-527.

Evans, R. Scott et al., "Evaluation of a Computer-Assisted Antibiotic-Dose Monitor," *The Annals of Pharmacotherapy*, vol. 33, Oct. 1999, pp. 1026-1031.

Evans, R. Scott, et al., "Development Of An Automatic Antibiotic Consultant," *M.D. Computing*, vol. 10, No. 1, 1993, pp. 17-22.

Evans, R. Scott et al., "A Computer-Assisted Management Program For Antibiotics and other Antiinfective Agents," *The New England Journal of Medicine*, vol. 338, No. 4, Jan. 22, 1998, pp. 232-239.

Evans, R. Scott, et al., "Prevention of Adverse Drug Events through Computerized Surveillance," pp. 437-441.

Evans, R. Scott, et al., "A Decision Support Tool for Antibiotic Therapy," pp. 651-655.

Evans, R. Scott, "Development of a Computerized Infectious Disease Monitor (CIDM)," *Computers and Biomedical Research*, vol. 18, 1985, pp. 103-113.

Fiocchi, R et al., "A Neural Support to the Prognostic Evaluation of Cardiac Surgery," pp. 435-436.

Goldberg, Dean E., et al., "Computer-based Program For Identifying Medication Orders Requiring Dosage Modification Based On Renal Function," *AJHP*, vol. 48, Sep. 1991, pp. 1965-1969.

Grimson, Jane B, "Integrating Knowledge-based Systems and Databases," *Clinica Chimica Acta*, 1993, vol. 222, pp. 101-115.

Grossi, Eugene A., et al., "Use of Artificial Intelligence to analyze clinical database reduces workload on surgical house staff," *Surgery*, vol. 116, No. 2, pp. 250-254, Aug. 1994.

Habbema, "Chapter 18: Predictive Tools for Clinical Decision Support," Handbook of our Medical Informatics, pp. 292-305.

Hamamoto, Isao et al., "Prediction of the Early Prognosis of the Hepatectomized Patient with Hepatocellular Carcinoma with a Neural Network," *Computer Bio Med.*, vol. 25, No. 1, 1995, pp. 49-59.

Hammond, Peter, "OaSiS: Integrating safety reasoning for decision support in oncology," pp. 185-191.

Harber, Philip et al., "An Expert System Based Preventive Medicine Examination Adviser," *JOEM*, vol. 37, No. 5, May 1995, pp. 563-570.

Henry, Suzanne Bakken et al., "A Template-based Approach to Support Utilization of Clinical Practice Guidelines Within an Electronic Health Record," *Journal of the American Medical Informatics Association*, vol. 5, No. 3, May/Jun. 1998, pp. 237-244.

Heras, J., et al., "TKR-tool: An Expert System for Total Knee Replacement Management," pp. 444-446, available on information and belief at least as early as 1994.

Hripcsak, George et al., "The Columbia-Presbyterian Medical Center Decision-Support System as a Model for Implementing the Arden Syntax," *Proceedings of the Annual Symposium on Computer Applications in Medical Care*, 1991, pp. 248-252.

Hunt, Dereck et al., "Effects of Computer-Based Clinical Decision Support Systems on Physician Performance & Patient Outcomes," *JAMA*, vol. 280, No. 15, Oct. 21, 1998, pp. 1339-1346.

James, Brent C., et al., "Making It Easy To Do It Right," *The New England Journal of Medicine*, vol. 345, No. 13, Sep. 27, 2001, pp. 991-993.

Johansson, Bo et al., "Arden Syntax As A Standard For Knowledge Bases In The Clinical Chemistry Laboratory," Clinica Chimica Acta 222, 1993, pp. 123-128.

Johnston, Mary E., et al., "Effects of Computer-based Clinical Decision Support Systems on Clinician Performance and Patient Outcome—A Critical Appraisal of Research," *Annals of Internal Medicine*, vol. 120, No. 2, Jan. 15, 1994, pp. 135-142.

Kahan, B.D., "Frontiers For the Coming Millennium," *Transplantation Proceedings*, vol. 28, No. 4, (Aug. 1996), pp. 2299-2306.

Kahn, Charles E, Jr., "Artificial Intelligence in Radiology: Decision Support Systems," *RadioGraphics*, Jul. 1994, vol. 14, No. 4, pp. 849-861.

Kahn, Charles E, Jr., et al., "Case-based Reasoning and Imaging Procedure Selection," *Investigative Radiology*, vol. 29, No. 6, Jun. 1994, pp. 643-647.

Kahn, Charles E., Jr., "Planning Diagnostic Imaging Work-up Strategies using Case-Based Reasoning," pp. 931-935.

Kanoui, Henry et al., "A Knowledge-Based Modeling Hospital Information Systems Components," pp. 319-330.

Ketcherside, W. Joseph et al., "Prediction of Survival In Trauma Patients using Probabilistic Neural Networks," 4 pages.

Ketikidis, P.H., et al., "ARRES: Computer Assisted Post Anesthesia Care Unit Monitoring System," *IEEE Engineering In Medicine & Biology Society 11th Annual International Conference*, pp. 1855-1856, available on information and belief at least as early as 1989.

Kindler H., et al., "An Advisor for the Management of the Acute Radiation Syndrome," pp. 386-396.

Kuperman, Gilad J., et al., "Detecting Alerts, Notifying the Physician, and Offering Action Items: A Comprehensive Alerting System," pp. 704-708, available on information and belief at least as early as 1996.

Kuperman, Gilad J., HELP: A Dynamic Hospital Information System, 1991, Springer-Verlag New York Inc., ISBN 0-387-97431-8, pp. 1-13, 34-52.

Kuperman, Gilad J., et al., "Representing Hospital Events as Complex Conditionals," pp. 137-141, available on information and belief at least as early as 1995.

Larsen, Robert A., et al., "Improved Perioperative Antibiotic Use and Reduced Surgical Wound Infections Through use of Computer Decision Analysis," *Infect Control Hospital Epidemiol*, vol. 10, No. 7, 1989, pp. 316-320.

Leão, Beatriz De F., et al., "Hycones: A Hybrid Approach to Designing Decision Support Systems," *MD Computing*, vol. 13, No. 2, 1996, pp. 160-164.

Lee, Susan Ciarrocca, "Using a Translation—Invariant Neural Network to Diagnose Heart Arrhythmia," *IEEE Engineering in Medicine & Biology Society 11th Annual International Conference*, pp. 2025-2026, available on information and belief at least as early as 1989.

Lehmann, E.D., et al., "Combining Rule-based reasoning and mathematical modelling in diabetes care," Artificial Intelligence in Medicine 6 (1994), pp. 137-160.

Lette, Jean et al., "Artificial Intelligence Versus Logistic Regression Statistical Modelling to Predict Cardiac Complications after Noncardiac Surgery," *Clin. Cardiol*, vol. 17, Nov. 1994, pp. 609-614.

Li, Yu-Chuan, et al., "Assessing the Behavioral Impact of a Diagnostic Decision Support System," 1995, pp. 805-809.

Lin, Kang-Ping, et al., "Classification of QRS Pattern by an Associative Memory Model," *IEEE Engineering in Medicine & Biology Society 11th Annual International Conference*, pp. 2017-2018, available on information and belief at least as early as 1989.

Maceratini, R., et al., "Expert Systems and the Pancreatic Cancer Problem: decision support in the pre-operative diagnosis," *J. Biomed. Eng.*, Nov. 1989, vol. 11. pp. 487-510.

Maclin, Phillip S., et al., "How to Improve a Neural Network for Early Detection of Hepatic Cancer," *Cancer Letters*, vol. 77, 1994, pp. 95-101.

Mann, N. Horace, III, et al., "Artificial Intelligence in the Diagnosis of Low Back Pain," *Orthopedic Clinics of North America*, vol. 22, No. 2, Apr. 1991, pp. 303-314.

Matisoff, Marty, "Cybernetics, Artificial Neural Networks & Medicine," *Journal of Clinical Engineering*, vol. 20, No. 6, Nov./Dec. 1995, 7 pages.

McCauley, Nancy, et al., "The Use of Expert Systems in the Healthcare Industry," *Information & Management*, vol. 22, 1992, pp. 227-235.

McDonald, Clement J., et al., "The Promise of Computerized Feedback Systems for Diabetes Care," *Ann Intern Med*, vol. 124, 1996, pp. 170-174.

Metzger, Jane, et al., "Clinical Decision Support for the Independent Physician Practice," *ihealthreports*, California HealthCare Foundation, First Counseling Group, Oct. 2002, pp. 1-41.

Molino, G., et al., "Design of Computer-assisted Programme Supporting The Selection and Clinical Management of Patients Referred for Liver Transplantation," *Ital J Gastroenterol*, vol. 26, 1994, pp. 31-43.

Monane, Mark, et al., "Improving Prescribing Patterns for the Elderly Through an Online Drug Utilization Review Intervention: A System Linking the Physician, Pharmacist, and Computer," *JAMA*, vol. 280, No. 14, Oct. 14, 1998, pp. 1249-1252.

Musen, Mark A., et al., "A Component-Based Architecture for Automation of Protocol-Directed Therapy," pp. 3-13.

Musen, Mark A., "Medical Informatics: Computer Applications in Health Care and Biomedicine," Chapter 16: Clinical Decision—Support Systems, pp. 572-609.

Musen, Mark A., et al. "A Rational Reconstruction of INTERNIST—I using Protégé-II," pp. 289-293, available on information and belief at least as early as 1995.

Pestotnik, Stanley L., et al., "Implementing Antibiotic Practice Guidlines through Computer-Assisted Decision Support: Clinical and Financial Outcomes," *Annals of Internal Medicine*, vol. 124, No. 10, May 15, 1996, pp. 884-890.

Pestotnik, Stanley L., et al., "Prospective Surveillance of Imipenem/Cilastatin Use and Associted Seizures Using a Hospital Information System," *The Annals of Pharmacotherapy*, vol. 27, Apr. 1993, pp. 497-501.

Pestonik, Stanley L., et al., "Therapeutic Antibiotic Monitoring: Surveillance Using a Computerized Expert System," *The American Journal of Medicine*, vol. 88, Jan. 1990, pp. 43-48.

Pietka, Ewa, "Neutal Nets for ECG Classification," *IEEE Engineering in Medicine & Biology Society 11th Annual International Conference*, pp. 2021-2022, available on information and belief at least as early as 1989.

Pryor, T. Allan, et al., "Sharing MLM's: An Experiment Between Columbia-Presbyterian and LDS Hospital," *Proceedings—The Annual Symposium on Computer Applicaitons in Medical Care*, pp. 399-403, available on information and belief at least as early as 1994.

Pryor, T. Allan, "The Help Medical Record System," *M.D. Computing*, 1988, vol. 5, No. 5, pp. 22-33.

Pryor, T. A., et al., "The HELP System," Journal of Medical Systems, vol. 7, No. 2, 1983, pp. 87-102.

Raschke, Robet A., et al., "A Computer Alert System to Prevent Injury From Adverse Drug Events: Development and Evaluation in a Community Teaching Hospital," *JAMA*, vol. 280, No. 15, Oct. 21, 1998, pp. 1317-1320.

Rector, Al, et al., "Shedding Light on Patients' Problems: Integrating Knowledge Based Systems Into Medical Practice," pp. 531-534.

Sabbatini, Renato M. E., "Using Neural Networks for Processing Biologic Signals," *Computing in Brazil*, pp. 152-159.

Safran, Charles, et al., "Development of a Knowledge-based Electronic Patient Record," *MD Computing*, vol. 13, No. 1, 1996, pp. 46-54, 63.

Saranummi, Niilo, et al., "Knowledge-based Systems in Medicine—a Nordic Research and Development Programme," *Computer Methods and Programs in Biomedicine*, vol. 34, 1991, pp. 81-89.

Schiff, Gordon D., et al., "Computerized Prescribing: Building the Electronic Infrastructure for Better Medication Usage," *JAMA*, vol. 279, No. 13, Apr. 1, 1998, pp. 1024-1029.

Schioler, Thomas, et al., "Information Technology Factors in Transferability of Knowledge-based systems in Medicine," *Artificial Intelligence in Medicine*, vol. 6, 1994, pp. 189-201.

Schloerb, Paul R., "Electronic Parenteral and Enteral Nutrition," *Journal of Parenteral and Enteral Nutrition*, Feb. 2000, vol. 24, No. 1, pp. 23-29.

Schmidt, R., et al., "Adaptation and Abstraction in a Case-based Antibiotics Therapy Adviser," pp. 209-217.

Shabot, M. Michael, et al., "Inferencing Strategies for Automated ALERTS on Critically Abnormal Laboratory and Blood Gas Data," 4 pages.

Shahar, Yuval, "Automated Support to Clinical Guidelines and Care Plans: The Intention—Oriented View," pp. 1-6.

White, Stuart C., "Decision-support Systems in Dentistry," *Journal of Dental Education*, vol. 60, No. 1, Jan. 1996, pp. 47-63.

Shortliffe, Edward H., "The Adolescence of AI in Medicine: Will the field come of age in the '90s?*," *Artificial Intelligence in Medicine*, vol. 5, 1993, pp. 93-106.

Sinnott, Margaret M., et al., "Knowledge based lipid management system for general practitioners," *Clinica Chimica Acta*, vol. 222, 1993, pp. 71-77.

Sondak, V. K., et al., "New Directions for Medical Artificial Intelligence," *Computers Math. Applic.*, vol. 20, No. 4-6, 1990, pp. 313-319.

Speight, P.M., "The Use of Artificial Intelligence to Identify People at Risk of Oral Cancer and Precancer," *Br. Dental*, vol. 179, 1995, pp. 382-387.

Stefanelli, Mario, "European Research Efforts in Medical Knowledge-based Systems," *Artificial Intelligence in Medicine*, vol. 5, 1993, pp. 107-124.

Xue, Qiuzhen, et al., "A Neural Network Weight Pattern study with ECG Pattern Recognition," *IEEE Engineering in Medicine & Biology Society 11th Annual International Conference*, pp. 2023-2024, available on information and belief at least as early as 1989.

Szolovits, Peter, et al., "Categorical and Probabilistic Reasoning in Medicine Revisited," *Artificial Intelligence*, vol. 59, 1993, pp. 167-180.

Tang, Paul, C., et al., "ActiveGuidelines: Integrating Web-Based Guidelines with Computer-Based Patient Records," 5 pages.

Thoreux, P.H., et al., "A Microcomputer Teaching and Decision-Support System for Emergency Medicine: Use of Hypermedia and Artificial Intelligence in Combination," *Med. Inform.*, vol. 21, No. 1, 1996, pp. 35-43.

Tierney, William M., et al., "Computerizing Guidelines to Improve Care and Patient Outcomes: The Example of Heart Failure," *JAMIA*, vol .2, No. 5, Sep./Oct. 1995, pp. 316-322.

Tong, D.A., et al., "WEANPRO: A Weaning Protocol Expert System," *IEEE Engineering In Medicine & Biology Society 11th Annual International Conference*, pp. 1857-1858, available on information and belief at least as early as 1989.

Torasso, Pietro, "A Report on Medical Expert Systems Research in Italy," *Artificial Intelligence in Medicine*, vol. 2, 1990, pp. 43-53.

Uckun, Serdar, "Artificial Intelligence in Medicine: State-of-the-art and Future Prospects," *Artificial Intelligence in Medicine*, vol. 5, 1993, pp. 89-91.

Van Bemmel, J.H., "Handbook of Medical Informatics," Houten/Diegem, 1997, pp. 232-260.

Van Dyne, M. M., et al., "Using Machine Learning and Expert Systems to Predict Preterm Delivery in Pregnant Women," pp. 344-350, available on information and belief at least as early as 1994.

Wagner, Michael M., "Clinical Event Monitoring at the University of Pittsburgh," 6 pages.

Wang, Shengrui, et al., "An Intelligent Interactive Simulator of Clinical Reasoning in General Surgery," pp. 419-423.

Wolfram, D.A., "An Appraisal of INTERNIST-I," *Artificial Intelligence in Medicine*, vol. 7, 1995, pp. 93-116.

Zhao, Y. K., et al., "Design and Development of an Expert System to Assist Diagnosis and Treatment of Chronic Hepatitis Using Traditional Chinese Medicine", *Med. Inform.*, vol. 19, No. 1, 1994, pp. 37-45.

"ADE Assistant." www.theradoc.com. Nov. 13, 2005. <http://www.theradoc.com/products/products_ade.html>.

"Antibiotic Assistant—Antibiotic Assistant Overview." www.theradoc.com. Nov. 13, 2005. <http://www.theradoc.com/products/products_abxassist.html>.

"Antibiotic Assistant—Integrated Model." www.theradoc.com. Nov. 13, 2005. <http://www.theradoc.com/products/products_integrated.html>.

Bates DW, et al., "The Costs of Adverse Drug Events in Hospitalized Patients. Adverse Drug Events Prevention Study Group," *JAMA* 277.4 (Jan. 22, 1997): 1 <http://jama.ama-assn.org/cgi/content/abstract/277/4/307>.

Burke, JP, "Hospitals Enter the War Against Antibiotic Resistance," [editorial review] *Current Opinion on Infectious Diseases* 8 (1995): 269-271.

Burke JP, et al., "A Retrospective Analysis of Twice-daily Cefotaxime Compared to Convetional Therapy for the Treatment of Infections in a USA Hospital," *Diagn Microbial Infect Dis* 22 (1995):167-69.

Burke JP, et al., "Antibiotic Cycling: What Goes Around Comes Around," [editorial review] *Current Opinion in Infectious Diseases* 13 (2000): 367-69.

Burke JP, et al., "Antibiotic Resistance: The Combat Zone," [editorial review] *Current Opinion in Infectious Diesases* 11 (1998): 441-43.

Burke JP, et al., "Antibiotic Resistance-Systems Thinking, Chaos and Complexity Theory," [editorial review] *Current Opinion in Infectious Diseases* 12 (1999): 317-19.

Burke JP, et al., "Breaking the Chain of Antibiotic Resistance," [editorial review] *Current Opinion in Infectious Diseases* 9 (1996): 253-55.

Burke JP, et al., "Evaluation of the Financial Impact of Ketorolac Tromethamine Therapy in Hospitalized Patients," Rpt. from *Clinical Therapeutics* 18.1 (1996): 197-211.

Burke JP, et al., "Evaluation of the Impact of Implementation of a Comprehensive Computerized Antibiotic Management Program at Intermountain Health Care," Healthcare Information and Management Systems Society Proceedings 1 (1997): 18-24.

Burke JP, et al., "Evaluation of Therapeutic Antibiotic Substitution by Microcosting Using an Automated Hospital Database," Abstracts of the 1991 ICAAC, The 31st Interscience Conference on Antimicrobial Agents and Chemotherapy. Chicago, IL (Sep. 29-Oct. 2, 1991), Article 407: 167.

Burke JP, et al., "Inappropriate Antibiotic Therapy: Detection Using Computer Algorithms," *Clinical Research* 36.1 (Jan. 1988): 28A.

Burke JP, et al., "The HELP System and Its Application to Infection Control," *Journal of Hospital Infection* 18(Supp. A) (1991): 424-31.

Burke JP, et al., "The Pharmacy and Drug Usage," *Assessing Quality Health Care: Perspectives for Clinicians*. Baltimore: Williams & Wilkins (1991): 509-20.

Burke JP, "The Quality of Antibiotic Use and the Quality of Measuring It," [editorial review] *Current Opinion in Infectious Diseases* 10 (1997: 289-291.

Burke JP, et al., Reply to Letters. *JAMA* 277.17 (May 7, 1997): 1351-1353.

Classen DC, et al., "Adverse Drug Events in Hospitalized Patients: Excess Length of Stay, Extra Costs, and Attributable Mortality," *JAMA* 277.4 (Jan. 1997): 301-6.

Classen DC, et al., "Adverse Effects of Intravenous Erythromycin in Hospital Patients: Attributable Costs and Excess Length of Stay," Abstracts of the 36th ICAAC, American Society for Microbiology, New Orleans, Louisana, Session 112 (Sep. 15-18, 1996): Article N19: 296.

Classen DC, et al., "Antibiotic Prophylaxis and Surgical Wound Infections," [To the Editor:] *New England Journal of Medicine* 327.3 (Jul. 16, 1992): 205-206.

Classen DC, et al., "Case 12.1: LDS Hospital: Institution-Wide Antibiotic Management," *Transforming Health Care Through Information Case Studies*. NM Lorenzi, et al. Ed. Springer-Verlag, New York, NY (1995): 322-332.

Classen DC, et al., "Clinical and Financial Impact of Intravenous Erythromycin Therapy in Hospitalized Patients," *Annals of Pharmacotherapy* 33 (Jun. 1999): 669-73.

Classen DC, et al., "Clinical Evaluation of a Computerized Antibiotic Selection Program in a Large Teaching Hospital," Abstracts of the 1992 ICAAC, The 32nd Interscience Conference on Antimicrobial Agents and Chemotherapy. Anaheim, CA (Oct. 11-14, 1992), Article 532: 199.

Classen DC, et al., "Computerized Surveillance of Adverse Drug Events in Hospitalized Patients," *JAMA* 266.20 (Nov. 27, 1991): 2847-51.

Classen DC, et al., "Description of a Computerized Adverse Drug Event Monitor Using a Hospital Information System," *Hospital Pharmacy* 27 (Sep. 1992):774, 776-779, 783.

Classen DC, et al., "Intensive Surveillance of Midazolam Use in Hospital Patients and the Occurrence of Cardiorespiratory Arrest," 12.3 *Pharmacotherapy* (1992): 213-16.

Classen DC, et al., "Prophylactic Antibiotics Used to Prevent Surgical Wound Infections," *Clinical Practice Improvement: A New Technology for Developing Cost-Effective Quality Health Care*. New York: Faulkner & Gray (1994): 217-21.

Classen DC, et al., "Surveillance for Quality Assessment: IV. Surveillance Using a Hospital Information System," 12.4 *Infection Control and Hospital Epidemiology* (Apr. 1991): 239-44.

Classen DC, et al., "The Computer-Based Patient Record: An Essential Technology for Hospital Epidemology," *Hospital Epidemology and Infection Control* Ed. CG Mayhall, Williams & Williams. Baltimore, MD (1996): 123-137.

Classen DC, "The Impact of Managed Care and Capitation on the Practice of Infectious Disease: Strategies for Managing Critical Care," Abstracts—35th Interscience Conference on Antimicrobial Agents and Chemotherapy an Annual Meeting of the American Society for Microbiology San Francisco, CA (Sep. 17-20, 1995): Article S19: 352.

Classen DC, et al., "The Timing of Prophylactic Administration of Antibiotics and the Risk of Surgical-wound Infections," *New England Journal of Medicine* 326.5 (Jan. 30, 1992): 281-86.

Classen, DC, et al., "The Computer-Based Patient Record: An Essential Technology for Hospital Epidemiology," *Hospital Epidemiology and Infection Control 2E*. Ed. C. Glen Mayhall, Lippiacott Williams & Williams, Philadelphia, PA (1999): 141-154.

Evans RS, et al., "A Computerized Approach to Monitor Prophylactic Antibiotics," *Proc Annu Symp Comput Appl Med Care* 11 (1987): 241-45.

Evans RS, et al., " A Decision Support Tool for Antibiotic Therapy," *Proc Annu Symp Comput Appl Med Care* 19 (1995): 651-55.

Evans RS, et al., "Applications of Medical Informatics in Antibiotic Therapy," *Antimicrobial Susceptibility Testing* 349 (1994): 87-96.

Evans RS, et al., "Computer Surveillance of Hospital-Acquired Infections and Antibiotic Use," *JAMA* 256.8 (Aug. 22/29, 1986): 1007-1011.

Evans RS, et al., "Computerized Identification of Patients at High Risk for Hospital-Acquired Infections," *American Journal of Infection Control* 20.1 (Feb. 1992): 4-10.

Evans RS, et al., "Development of a Computerized Adverse Drug Event Monitor," *Proc Annu Symp Comput Appl Med Care* 15 (1991): 23-27.

Evans RS, et al., "Development of an Automated Antibiotic Consultant," *M.D. Computing* 10.1 (1993): 17-22.

Evans RS, et al., "Evaluating the Impact of Computer-based Drug Monitoring on the Quality and Cost of Drug Therapy," *Hospital Information Systems* (1995): 201-220.

Evans RS, et al., "Experience with a Computer-Assisted Antiinfective Agent Management Program," *Computer-Assisted Decision-Making Activated by Clinical Laboratory Findings. Clin Chem Lab Med* Symposium Abstracts—IFCC-WorldLab '99. Firenze. 37—Special Supplement (Jun. 6-11, 1999): S6.

Evans RS, et al., "Improving Empiric Antibiotic Selection Using Computer Decision Support," *Arch Intern Med* 154 (Apr. 25, 1994): 878-84.

Evans RS, et al., "Prediction of Hospital Infections and Selection of Antibiotics Using an Automated Hospital Database," *Proc Annu Symp Comput Appl Med Care* 14 (1990): 663-67.

Evans RS, et al., "Preventing Adverse Drug Events in Hospitalized Patients," *Annals of Pharmacotherapy* 28 (Apr. 1994): 523-527.

Evans RS, et al., "Prevention of Adverse Drug Events Through Computerized Surveillance," *Proc Annu Symp Copmut Appl Med Care* 16 (1992): 437-41.

Evans RS, et al., "Reducing the Duration of Prophylactic Antibiotics through Computer Monitoring of Surgical Patients," *DICP, The Annuals of Pharmacotherapy* 24 (Apr. 1990): 351-354.

Evans RS, et al., "The Evaluation of an Automated Antibiotic Consultant," National Technical Information Services, Departments of Medical Informatics, Infectious Diseases, and Pharmacy, LDS Hospital and University of Utah School of Medicine, Salt Lake City, UT (1994): 1-25.

Evans RS, et al., "Using a Hospital Information System to Assess the Effects of Adverse Drug Events," *Proc Annu Symp Comput Appl Med Care* 17 (1993): 161-65.

Gundlapalli AV, et al., "A Rule-based Computer System to Facilitate Public Health Surveillance: Deployment by a Hospital Infection Control Unit," upon information and belief, available at least as early as 2001.

Gundlapalli AV, et al., "Hospital Electronic Medical Record-Based Public Health Surveillance System Deployed During the 2002 Winter Olympic Games," Presented in part at the 2003 APIC Conference, San Antonio, TX, Session 2301 (Jun. 10, 2003): 1-17.

Harbarth S, et al., "Clinical and Economic Outcomes of Conventional Amphotericin B-Associated Nephrotoxicity," *CID* 35 (Dec. 15, 2002): e120-127.

Harbarth S, et al., "The Epidemiology of Nephrotoxicity Associated with Conventional Amphotericin B Therapy," *American Journal of Medicine* 111 (Nov. 2001): 528-534.

Hongsermeier TM, et al., "TheraDoc Expert Systems: The Cornerstone of a Successful Infection Management and Patient Safety Strategy," *White Paper*, Salt Lake City: TheraDoc, Inc. (2003): 1-10.

Kelly DL, et al., "Reengineering a Surgical Service Line: Focusing on Core Process Improvement," *American Journal of Medical Quality* 12.2 (1997): 120-29.

Larsen RA, et al., "Improved Perioperative Antibiotic Use and Reduced Surgical Wound Infections Through Use of Computer Decision Analysis," *Infect Control Hosp Epidemiol* 10.7 (1989): 316-320.

Leader WG, et al., "Integrating Pharmacokinetics into Point-of-Care Information Systems," *Clin. Pharmacokinet*. 31.3 (Sep. 1996): 165-173.

Lo TS., et al., "Secular Trends of Enterococcal Urinary Tract Infection: A Ten-Year Study [Abstract]," American Society for Microbiology, 1st International ASM Conference on Enterococci, available at least as early as Dec. 6, 1999: 1.

Naranjo CA, et al., "A Method for Estimating the Probability of Adverse Drug Reaction," *Clinical Pharmacology and Therapeutics* 30.2 (Aug. 1981): 239-245.

Pestotnick SL, et al., "Medical Informatics: Meeting the Information Challenges of a Changing Health Care System," *Journal of Informed Pharmacotherapy* 2 (2000): 1.

Pestotnik S, "The Future of ID Pharmacy Practice: Puttiing Decisions in Decision Support," [editorial] *Society of Infectious Diseases Pharmacists Newsletter* 5.3 (Fall 1995): 2-3.

Pestotnik SL, (Aug. 1993). "Computer-Based Alerts for Drug Dosing in Renal Impairment," unpublished masters thesis, University of Utah, Salt Lake City, Utah, United States: 1-62.

Pestotnik SL, "Role of Information Systems in Reducing Adverse Drug Events," *Improving the Quality of the Medication Use Process: Error Prevention & Reducing Adverse Drug Events*. New York: Pharmaceutical Products Press/Haworth Press, Inc. (1998): 183-91.

Pestotnik SL, et al., "A Five-Year Analysis of Parental Anti-infective Use at a Teritary Care Hospital," Abstracts of the 33rd ICAAC. New Orleans, LA (Oct. 17-20, 1993), 634: 235.

Pestotnik SL, et al., "Adverse Effects of Intravenous Vancomycin (IVV) in Hospital Patients: Attributable Costs and Excess Length of Stay," *Clinical Infectious Diseases*, Abstracts of the IDSA 35th Annual Meeting 25.2 (Aug. 1997) Article 376: 424.

Pestotnik SL, et al., "Expert Clinical Decision Support Systems to Enhance Antimicrobial Stewardship Programs," *Pharmacotherapy* 25.8 (2005): 1116-25.

Pestotnik SL, et al., "Expert Clinical Decision Support Systems to Enhance Antimicrobial Stewardship Programs," *Society of Infectious Diseases Pharmacists Newsletter* 14.3 (Winter 2005): 2-7.

Pestotnik SL, et al., "Medical Informatics, Decision Support, and Quality of Care: Clinician's Perspective," *International Pharmaceutical Abstracts*, Information Processing and Literature, 3505425: 817.

Pestotnik SL, et al., "Prospective Surveillance and Imipenem/Cilastatin Use and Associated Seizures Using a Hospital Information System," *Annals of Pharmacotherapy* 27 (Apr. 1993): 497-501.

Pestotnik SL, et al., "Surveillance of Imipenem-associated Seizures in a Large Cohort of Hospitalized Patients," Abstracts of the 1992 ICAAC, The 32nd Interscience Conference on Antimicrobial Agents and Chemotherapy, Anaheim, CA (Oct. 11-14, 1992), 530: 199.

Pestotnik SL, et al., "Therapeutic Antibiotic Monitoring: Surveillance Using a Computerized Expert System," *American Journal of Medicine* 88 (Jan. 1990): 43-48.

Riley DK, et al., "The Effect of Improved Prophylactic and Therapeutic Antibiotic Use on Hospital Microbial Resistance Patterns," *Infection Control and Hospital Epidemiology*, S2 (Apr. 1994): P26.

Tettelbach W, et al., "Usage Evaluation of a Computerized Clinical Decision Support System (CDSS) Utilized by the Rural Antibiotic Decision-Support & Resistance (RADAR) Project," upon information and belief, available at least as early as 2001.

Pestotnik SL, "E-Prescribing in the Hospital with the Theradoc System," 44th Interscience Conference on Antimicrobial Agents and Chemotherapy. Washington, DC (Oct. 30-Nov. 2, 2004), (abst. 636).

Classen DC, et al., "Antibiotic Outcomes Research: A Large Randomized Trial of Cephalosporin Use in Hospitalized Patients," *Clin. Res*. 39.2 (1991): 373A.

Tettlebach WH, et al., "Usage Evaluation of a Web-based Computerized Clinical Decision Support System," 42nd ICAAC Abstracts, 42nd Interscience Conference on Antimicrobial Agents and Chemotherapy. San Diego, CA (Sep. 27-30, 2002), (abst. W-1159).

An Update from IHCNET, Help's Pharmacy System, vol. 1, No. 4, pp. 1-3, Jul./Aug. 1989.

Bleich, Howard L. et al., Clinical Computing in a Teaching Hospital, The New England Journal of Medicine, pp. 756-764, Mar. 21, 1985.

Bleich, Howard L., The Computer as a Consultant, Seminars in Medicine of the Beth Israel Hospital, Boston, vol. 284, No. 3, pp. 141-147, Jan. 21, 1971.

Bradshaw, Karen E., et al., Development of a Computerized Laboratory Alerting System, Computers and Biomedical Research, 22 575-587 (1989).

Classen, David C. et al., Surveillance for Quality Assessment: IV. Surveillance Using a Hospital Information System, Infection Control and Hospital Epidemiology, vol. 12, No. 4, pp. 239-244, Apr. 1991.

Gardner, Reed M., Computerized Data Management and Decision Making in Critical Care, Surgical Clinics of North America, vol. 65, No. 4, pp. 1041-1051, Aug. 1985.

Kennedy, Dianne L. et al., Monitoring of Adverse Drug Events in Hospitals, JAMA, p. 2878, Nov. 27, 1991.

McDonald, Clement J. et al., The Regenstrief Medical Records, M.D. Computing, vol. 5, No. 5, pp. 34-47, 1988.

Pazzani, Michael J. et al., Application of an Expert System in the Management of HIV-Infected Patients, Journal of Acquired Immune Deficiency Syndromes and Human Retrovirology, vol. 15, No. 5, pp. 356-362, 1997.

Pryor, T. Allan, Development of Decision Support Systems, International Journal of Clinical Monitoring and Computing 7:137-146, 1990.

Stead, William W. et al., Computer-Based Medical Records: The Centerpiece of TMR, M.D. Computing, vol. 5, No. 5, pp. 48-61, 1988.

Yu et al., Antimicrobial Selection by a Computer, A Blinded Evaluation by Infection Disease Expers, JAMA, vol. 242, No. 12, pp. 1279-1282, Sep. 21, 1979.

Evans R. Scott, et al., "Evaluating the Impact of Computer-based Drug Monitoring on the Quality and Cost of Drug Therapy," *Hospital Information Systems: Design and Development Characteristics: Impact and Future Architecture*. Medical Artificial Intelligence Series. Amsterdam: Elsevier. 2 (1998): 1-20.

* cited by examiner

SYSTEMS AND METHODS FOR COMMUNICATING BETWEEN A DECISION-SUPPORT SYSTEM AND ONE OR MORE MOBILE INFORMATION DEVICES

BACKGROUND OF THE INVENTION

1. The Field of the Invention

This invention relates to decision-making processes where information is analyzed to provide an individual with one or more suggested solutions or actions. More specifically, the present invention relates to transferring and synchronizing medical data between a decision-making medical system and one or more mobile information devices used by clinicians, thereby aiding a clinician to more efficiently treat patients than is currently possible.

2. The Prior State of the Art

The U.S. health care delivery system has undergone breathtaking changes since the late 1980's. Escalating costs, diminishing resources, demands for accountability characterize today's medical marketplace, inescapable conflicts regarding meaningful outcomes measures, and an expanding medical knowledge base.

Health care is an information intensive industry and the delivery systems typically used within hospitals and clinics are drowning in data while starving for information. It is no exaggeration to describe the current health care delivery system as undergoing an information revolution. Increasingly providers and health care researchers experience demands for more accurate and accessible information. The complexity of health care, its burgeoning information base, and the turbulence of the medical marketplace have all contributed to a system grappling with methods to efficiently synthesize and disseminate information, standardize care, and to continue to create and innovate. The obstacles to these goals are the same regardless of whether the health care delivery entity is a small hospital, long-term/skilled nursing facility, medical clinic, home health agency, hospice, emergent care unit, or large institution. The frustrations and barriers are faced equally whether the affiliation is academic public or private, managed care or fee-for-service, not-for-profit or for profit. All entities are faced with the need to identify strategies and solutions to manage information and make better decisions, whether those decisions are medical or business-related in nature.

Of particular interest to the demands of the ever increasing need for more accurate and accessible information is the area of clinical decision-making. Clinical decisions are of particular interest since they often influence the balance of human suffering and well-being. Clinical decisions, not unlike all human decisions, are complex and influenced by many causal relationships. These relationships include the evidence-base of medicine, patient-physician factors and interactions, and external and internal constraints. Whether clinicians are serving individual patients or populations they have always sought to base their decisions on the best available evidence. This simple tenet has been confounded by the continual expansion of medicine's evidence-base. The rapid expansion of the scientific and clinical evidence has changed the health care landscape so that no longer is the question how much of medical practice is based in evidence, but rather how much of the available evidence is applied at the front lines of patient care.

One front line of patient care involves the daily visit of a clinician to each patient under he or she's care, commonly termed "rounds". A clinician, or subordinate clinician, visits each patient and views the current medical condition of the patient, typically, represented by vital statistics and other information contained within paper charts. Commonly, the subordinate clinician must prepare to report the progress of the patient by providing a medical history of the patient and current medical information, with suggested treatments. The "rounds" process is time consuming and complex since each patient will typically have different medical conditions influenced by a large number of different factors, such as demographics, family history or genetic background, occupational influences, and the like. To properly diagnose and treat each patient a clinician and/or subordinate clinicians must understand the nuances of the medical condition of each patient, and respond accordingly to variations in the current medical condition of the patient. Additionally, the clinician and subordinate clinician must maintain his or her knowledge base with the ever-changing medical and scientific knowledge base.

Although clinicians maintain a high knowledge base of medical information, clinician's are human and sometimes may not recognize signals or medical information that suggests a medical condition unrelated to the medical condition for which the patient was admitted. Such error in judgment or misinterpretation of medical information may result in increased patient stay in the medical facility or possibly patient death.

Clinicians are, therefore, influenced by a number of complex and varied constraints during the decision-making process of how to treat a patient's medical condition. Such constraints involve the factors of time, community standards, formal policies and laws, and the issues of reimbursement. Add to these constraints the need to for the clinician to maintain his or her knowledge base with the ever-changing medical and scientific knowledge base, and it is obvious that clinicians attempt to make informed medical decisions under difficult conditions.

It would be an advance to provide methods and systems to aid the clinician in providing an informed and accurate medical decision for each specific patient under his or her care that has a basis in the most current medical and scientific knowledge.

SUMMARY OF THE INVENTION

It is an object of the present invention to provide a system and method for accessing medical information in an efficient and controllable manner.

It is another object of the present invention to provide a system and method for presenting a clinician with medical information in a manner controlled by the clinician.

Another object of the present invention is to provide a system and method that conveys medical information in a concise manner that aids a clinician in diagnosing and treating medical conditions.

Yet another object of the present invention is to provide a system and method for summarizing the current medical status of a patient based upon the most current medical information and the patient's previous medical history.

Still yet another object of the present invention is to provide a system and method for synchronizing the medical information gathered by a clinician with existing medical information of the patient.

Another object of the present invention is to provide a system and method for updating a personal digital assistant with summarized patient data specific to those patient's that a clinician is to examine within and definable period of time.

Yet another object of the present invention is to provide a system and method to synchronize proscribed medications and administered treatments with the various related departments within a medical facility.

Still yet another object of the present invention is to provide a system and method to allow real-time communication between a decision supporting system and a clinician to aid the clinician in making informed decisions related to patient medical care.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims. These and other objects of the present invention will become more fully apparent from the following description and appended claims, or may be learned by the practice of the invention as set forth hereinafter.

As disclosed previously, clinicians are influenced by a number of complex and varied constraints during the decision-making process of how to treat multiple patients each having varied medical conditions. Each clinician must maintain a large personal knowledge base to provide medical care to a variety of different patients with varied family histories and backgrounds. Although clinicians typically educate themselves, during the rigors of the performing medical care, such knowledge may not raise to the clinician's memory. To achieve the foregoing objects, and in accordance with the invention as embodied and broadly described herein, systems and methods for providing clinicians with recommended and suggested medical care that is based upon a large expert knowledge base and specific to each patient that a clinician may visit, termed decision-support patient data, is disclosed.

In one embodiment, a method for delivering decision-supported patient data of a patient to a user module accessible by a clinician in a controlled and repeatable manner is disclosed. The method includes the steps of analyzing patient data to identify current patient data of each patient that a clinician is to examine in a defined time period. Such current patient data may include general health information like blood pressure and heart rate and/or medical condition specific data such as blood sugar level for a diabetes patient.

The current patient data is evaluated with the expert knowledge of a knowledge base to generate decision-supported patient data for each patient that is to be examined within the defined time period. As referenced-above, the decision-supported patient data provides the clinician with potential medical conditions that the patient may have and recommendations for medical care.

Once the current patient data and other medical history data and information are evaluated, the decision-supported patient data is presented to the clinician in a configuration that assists the clinician in treating each patient. The displayed data provides the clinician with the pertinent information related to the patient's existing and potential medical condition and the medical care to be implemented by the clinician. For example, the display may include warnings related to a particular recommended treatment for a specific patient.

Such method may be performed in real-time so that the clinician may receive updated decision-supported patient data from a decision-support module and/or medical module. In this manner the clinician is aided in making informed decisions related to patient medical care.

One of the modules implemented by one embodiment of the present invention is a decision-support module. The decision-support module generates decision-supported patient data specific to each patient that a clinician is to examine in a defined time period. The decision-support module includes a knowledge module that stores data representative of expert knowledge within the medical field. Such expert knowledge is gleaned from various sources and experts in a variety area of the medical field. The decision-support module also includes a patient module that stores patient specific data. Communicating with the knowledge module and the patient module is an inference engine that generates the decision-supported patient data based upon the information and data stored in the knowledge module and the patient module.

Another module of the present invention is a user module. The user module communicates with the decision-support module and allows the decision-supported patient data to be presented to the clinician in a configuration that assists the clinician in treating each patient. The user module may have various other modules that allow the decision-supported patient data and other patient specific data to be stored therein and accessed by the clinician as a clinician makes a determination as to the medical care to proscribe for each patient that the clinician examines.

In this manner, the present invention is capable of using various user modules to effectively provide decision-supported patient data to a clinician in a configuration that assists the clinician in making a decision related to medical care of a patient.

BRIEF DESCRIPTION OF THE DRAWINGS

In order that the manner in which the above-recited and other advantages and features of the invention are obtained, a more particular description of the invention briefly described above will be rendered by reference to specific embodiments thereof that are illustrated in the appended drawings. Understanding that these drawing depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention extends both methods and systems for updating and gathering data from a database through the use of hand held-technologies. The embodiments of the present invention may comprise a special purpose or general purpose computer including various other computer hardware and/or software modules and components, as discussed in greater detail below.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

Figure 1:
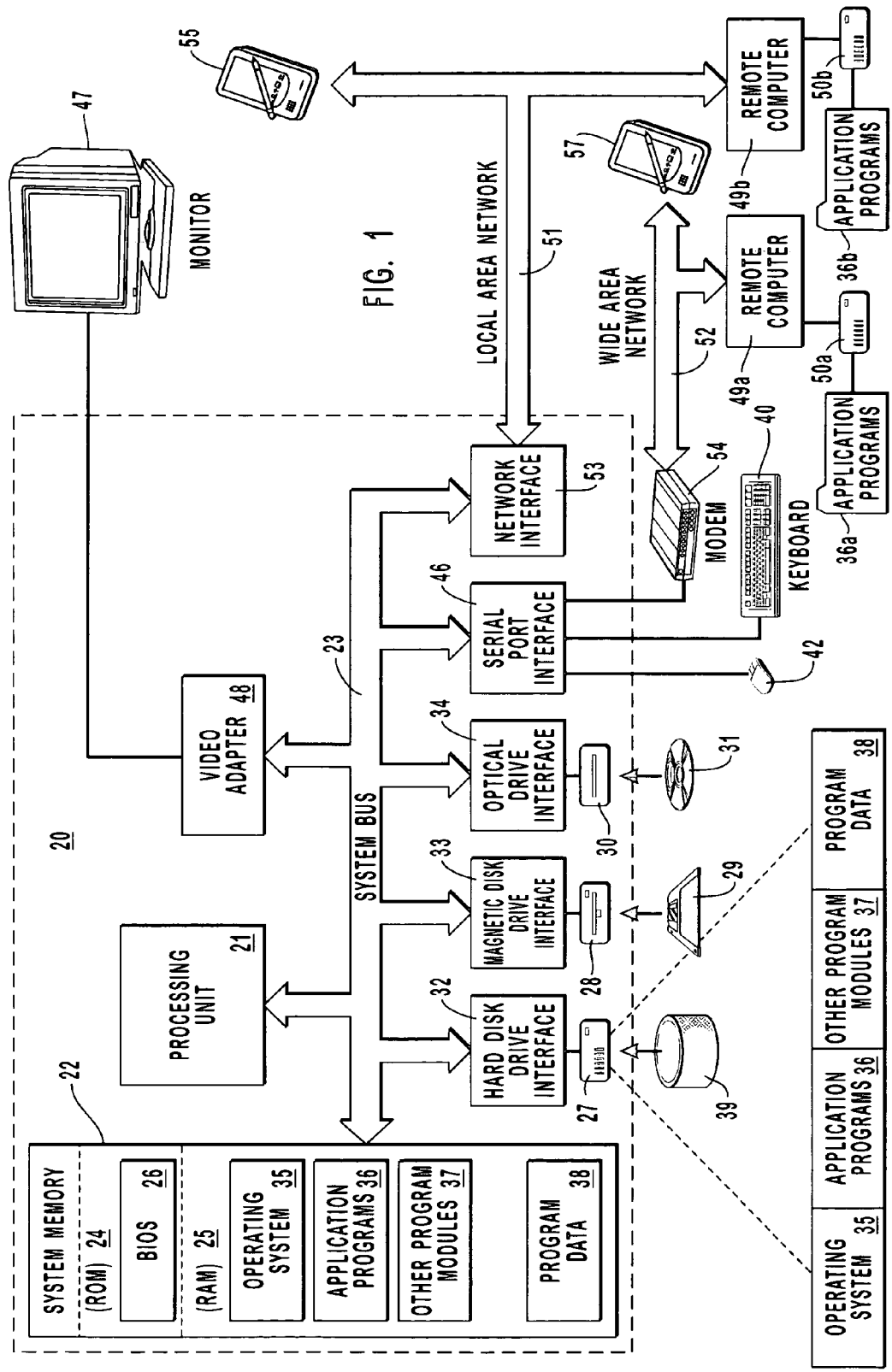
FIG. 1 illustrates an exemplary system that provides a suitable operating environment for the present invention.

FIG. 1 and the following discussion are intended to provide a brief, general description of a suitable computing environment in which the invention may be implemented. Although not required, the invention will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 1, an exemplary system for implementing the invention includes a general purpose computing device in the form of a conventional computer 20, including a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help transfer information between elements within the computer 20, such as during start-up, may be stored in ROM 24.

The computer 20 may also include a magnetic hard disk drive 27 for reading from and writing to a magnetic hard disk 39, a magnetic disk drive 28 for reading from or writing to a removable magnetic disk 29, and an optical disk drive 30 for reading from or writing to removable optical disk 31 such as a CD-ROM or other optical media. The magnetic hard disk drive 27, magnetic disk drive 28, and optical disk drive 30 are connected to the system bus 23 by a hard disk drive interface 32, a magnetic disk drive-interface 33, and an optical drive interface 34, respectively. The drives and their associated computer-readable media provide nonvolatile storage of computer-executable instructions, data structures, program modules and other data for the computer 20. Although the exemplary environment described herein employs a magnetic hard disk 39, a removable magnetic disk 29 and a removable optical disk 31, other types of computer readable media for storing data can be used, including magnetic cassettes, flash memory cards, digital video disks, Bernoulli cartridges, RAMs, ROMs, and the like.

Program code means comprising one or more program modules may be stored on the hard disk 39, magnetic disk 29, optical disk 31, ROM 24 or RAM 25, including an operating system 35, one or more application programs 36, other program modules 37, and program data 38. A user may enter commands and information into the computer 20 through keyboard 40, pointing device 42, or other input devices (not shown), such as a microphone, joy stick, game pad, satellite dish, scanner, or the like. These and other input devices are often connected to the processing unit 21 through a serial port interface 46 coupled to system bus 23. Alternatively, the input devices may be connected by other interfaces, such as a parallel port, a game port or a universal serial bus (USB). A monitor 47 or another display device is also connected to system bus 23 via an interface, such as video adapter 48. In addition to the monitor, personal computers typically include other peripheral output devices (not shown), such as speakers and printers.

The computer 20 may operate in a networked environment using logical connections to one or more remote computers, such as remote computers 49a and 49b. Additionally, computer 20 may communicate with one or more mobile information devices 55 and 57, such as personal digital assistant's (PDA), pagers, telephones, Black Berries, pocket PC's, consumer electronic devices, palm computers, and the like.

Remote computers 49a and 49b and mobile information devices 44 and 57 may each be another personal computer, a server, a router, a network PC, a peer device or other common network node, and typically includes many or all of the elements described above relative to the computer 20, although only memory storage devices 50a and 50b and their associated application programs 36a and 36b have been illustrated in FIG. 1. The logical connections depicted in FIG. 1 include a local area network (LAN) 51 and a wide area network (WAN) 52 that are presented here by way of example and not limitation. Such networking environments are commonplace in office-wide or enterprise-wide computer networks, intranets and the Internet.

When used in a LAN networking environment, the computer 20 is connected to the local network 51 through a network interface or adapter 53. When used in a WAN networking environment, the computer 20 may include a modem 54, a wireless link, or other means for establishing communications over the wide area network 52, such as the Internet. The modem 54, which may be internal or external, is connected to the system bus 23 via the serial port interface 46. In a networked environment, program modules depicted relative to the computer 20, or portions thereof, may be stored in the remote memory storage device. It will be appreciated that the network connections shown are exemplary and other means of establishing communications over wide area network 52 may be used.

The present invention is discussed herein with reference to a decision-support system where patient data and information is gathered and analyzed with stored patient data and information to generate decision-supported patient data. The system provides the clinician with the decision-supported patient data, or optionally and summarized versions of the decision-supported patient data, optionally in real-time or clinician perceived real-time. Although discussion is made to the use of the present invention in a decision-support system, it may be appreciated that the present invention is not limited to use with a decision-support system, but may be used in various other systems.

Figure 2:
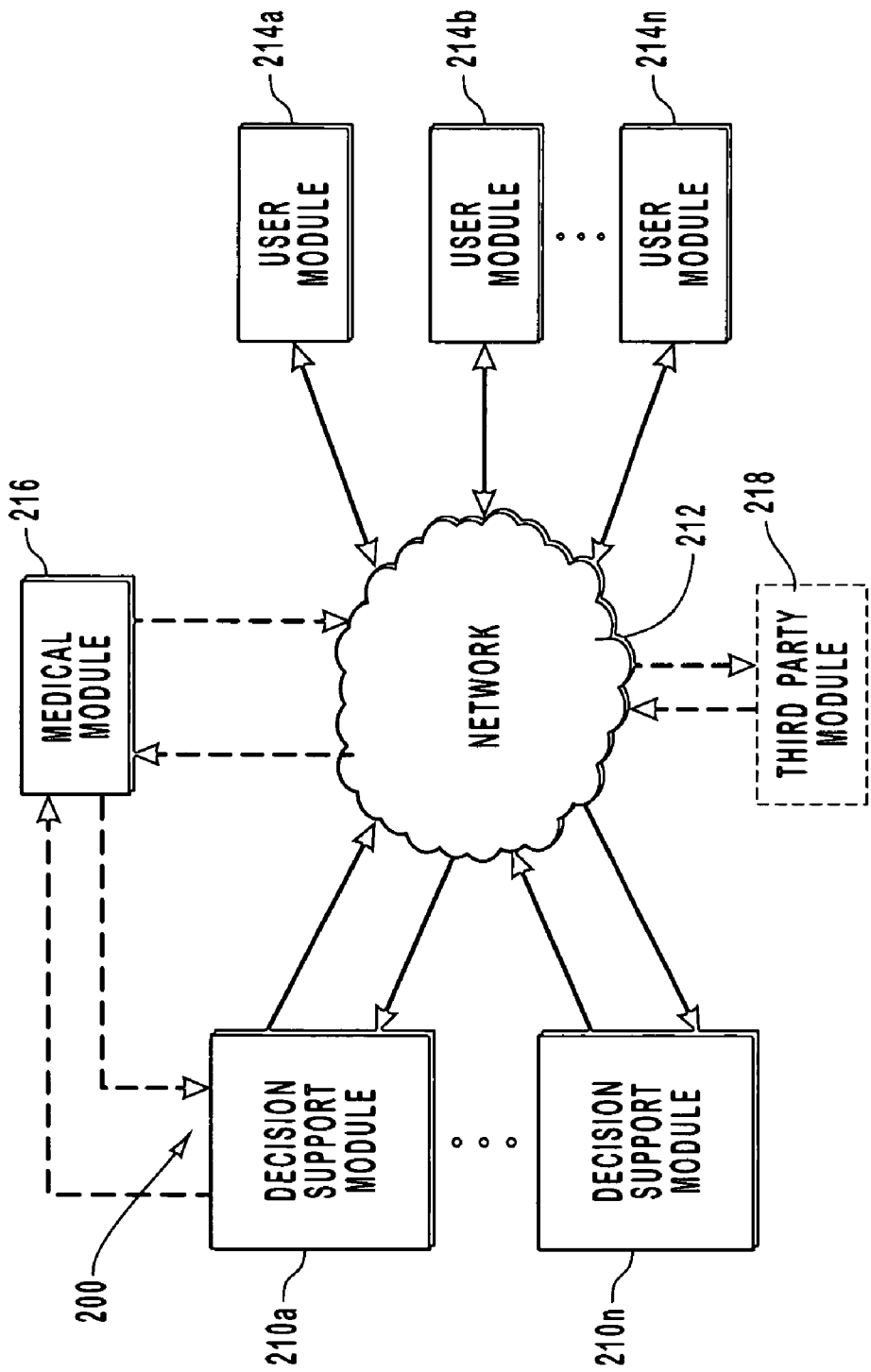
FIG. 2 is a schematic representation of one embodiment of the system of the present invention.

FIG. 2 is a block diagram illustrating a decision-support system implementing one embodiment of the present invention. As shown, system 200 includes one or more decision-support modules 201a-210n that communicate with one or more use modules 214a-214n via network 212. Optionally, as designated by dotted lines, system 200 may include a medical module 216 and a third party module with which decision-support modules 210a-210n and user modules 214a-214n may communicate. Additionally, medical module 216 and the third party module communicate one with another.

Through the configuration illustrated in FIG. 2, a patient or clinician may input information regarding the patient's health, medical conditions, billing information, and past and current medical care, termed "patient data". Subsequently, system 200 may evaluate this patient data to create data that assists the clinician in making a medical diagnosis or medical care decision. Such data is termed "decision-supported patient data."

Optionally, the decision-supported patient data may be configured in the form of a decision-supported progress note that assists the clinician in making a medical diagnosis of medical care decision. The decision-supported progress note is a module, data file, record, field, or one or more data storages that contain information and data that represents a qualitative and quantitative analysis of the patient assessment process performed by the decision-support module 210 and the clinician and the recommended plan of medical care suggested by decision-support module 210. Such qualitative and quantitative analysis may extend over a long period, such as with an outpatient situation, or over a shorter period, such as with an inpatient situation.

In this manner, system 200 may gather and analyze stored patient data with input patient data to generate decision-supported patient data, optionally, in real-time or perceived real time. Although discussion is made to the use of the present invention in a 1 decision-support system, it may be appreciated that the novel features of the present invention are not limited to use with a decision-support system but may be used in various other systems.

As illustrated in FIG. 2, system 200 includes decision-support module 210. Decision-support system 210, in one embodiment, allows a patient to store and access patient data, while allowing a clinician to store, update, and access the patient data and decision-supported patient data that contain information regarding the diagnosis and treatment of various medical conditions. Additionally, the clinician may access a knowledge base that includes data representative of the current expert medical knowledge within a variety of medial areas that assists the clinician with the diagnosis and medical care of the patient. The patient data, the decision-supported patient data, and the knowledge base need not be incorporated within decision-support module 210, but may be located remotely from decision-support module 210 and accessible by decision-support module 210. For example, optional medical module 216, as illustrated by dotted lines, may include one or more servers that store the patient data, the decision-supported patient data, and the knowledge base.

Facilitating communication between decision-support modules 210a-210n, user modules 214a-214n, and optionally medical module 216 is network 212. Network 212 may be a local area network (LAN) such as a hospital or clinic intranet, wide area network (WAN), wireless network, packetized network, real-time network, and various other networks known by one skilled in the art. Decision-support modules 210a-210n communicate with network 212 via various types of communication line connections, such as but not limited to, cable or cable modems, satellite, telephone lines, whether analog or digitally based, the internet, DSL, G-Lite, wireless technology, infra-red (IR) technology, other high-speed data connections, or any other suitable transmission technology or medium. One skilled in the art may identify various other types of network and/or communication line connections that are capable of performing the desired function of allowing decision-support modules 210a-210n to communicate with user modules 214a-214n and optionally medical module 216.

Each user module 214a-214n communicates with decision-support module 210 to allow a clinician or a patient to gather patient data and receive decision-supported patient data or progress notes in real-time or perceived real-time. For example, the clinician and/or patient may provide and receive data regarding the patient's general health, exercise, eating, smoking, drinking, and drug habits, if any, and the like, while the clinician may view current and past medical conditions, treatments, medications proscribed, family history, genetic predispositions and microbial susceptibilities, and the like. The clinician, therefore, may retrieve data from and transmit data to decision-support modules 210a-210n, optionally in real-time or perceived real-time and receive from decision-support modules 210a-210n medical diagnoses and medical care recommendations, optionally in real-time or perceived real-time.

As discussed herein, the operation of either transmitting data and/or receiving data, in various forms and types, shall be termed collectively as "transceiving" and transceiving data between decision-support module 210a-210n, user module 214a-214n, and medical module 216 without a substantial delay between an input and a response is real-time or perceived real-time communication.

The transceiving of patient data, decision-supported patient data, and decision-supported progress notes between decision-support module 210 and user modules 214a-214n is accomplished by synchronizing decision-support module 210 and user modules 214a-214n through a variety of communication line connections and synchronization manners, such as wireless synchronization, direct dial synchronization, desktop synchronization, or such others as known by one skilled in the art. Such synchronization may optionally be continuous, substantially continuous, periodic, sporadic, or the like.

Those skilled in the art will appreciate that each user module 214a-214n may take various configurations, including personal computers, hand-held devices, multi-processor systems, microprocessor-based or programmable consumer electronic devices, telephones, pagers, pocket PCs, network PCs, minicomputers, mainframe computers, and the like. Such devices and user module 214a-214n may be considered mobile information devices. Preferably, user module 214a-214n is a personal digital assistant (PDA). Generally, therefore, each user module 214a-214n may include the structure and functionality of computer 20 with associated application programs 36 and memory 22 to store the application programs 36 and medical data and information.

Optional medical module 216 represents the various hardware and software modules and components of a medical facility, such as a hospital, clinic, and the like. Each medical facility may store business data, medical data, patient data, decision-supported patient data, decision-supported progress notes, and the like. Medical module 216, in one embodiment, includes various modules associated with the medical facility's intranet or internal network that links various departments of a hospital or clinic. For example, the departments may include radiology, the pharmacy, administration, the laboratories, and the like. Additionally, medical module 216 may include the hardware and software modules and components for medical module 216 to communicate with decision-support module 210 and user modules 214a-214n by a communication line connection known to one skilled in the art in light of the teaching contained herein.

According to another aspect of the present invention, system 200 optionally includes third party module 218. The third party module represents the various other modules that may communicate with decision-support module 210, user modules 214a-214n, and medical module 216. For example, the third party module may represent a medical provider, an insurance carrier, a referred clinician, a referring clinician, a third party paging service, and the like. In this manner, a clinician may communicate with outside sources to obtain approval for services and/or give information to the outside sources. For example, system 200 may allow decision-support module 210 to communicate with an insurance carrier, health care management organization (HMO), or other similar health care provider to received authority to give a recommended medical treatment. One skilled in the art may identify various other third parties that may obtain benefits from the present invention.

Generally, the configuration of system 200 facilitates the gathering of patient data and delivery of decision-supported patient data to a clinician and patient. For example, if a clinician is examining a patient for the first-time, i.e. a new outpatient, one or more of decision-support modules 210a-210n analyze the medical information collected by system The resultant diagnosis, if any, is subsequently transmitted to user module 214a-214n. Additionally, decision-support modules 210a-210n transmit recommended treatments, procedures, tests, therapeutic drugs, and the like, which a clinician may use to treat the medical condition or prevent the onset of one or more other medical conditions. Furthermore, decision-support module 210a-210n may deliver educational materials that decision-support module 210a-210n identifies as appropriate for the patient, whether for general health purposes or for a specific medical condition. For example, if the current medical condition of the patient suggests a potential for heart disease or a heart attack in the future, decision-support module 210a-210n may generate educational literature directed to helping the patient to change their eating, smoking, drinking, and exercising habits to combat the potential for a heart attack or other heart related medical problems.

Alternatively, system 200 may be used in an "impatient" setting. Decision-support modules 210a-210n, therefore, may analyze the newly gathered patient data with the stored patient data relating to the patient's previous or preexisting medical conditions. Upon analyzing the relevant patient data decision-support modules 210a-210n deliver recommended treatments, procedures, tests, therapeutic drugs, and the like to the clinician. As with the outpatient situation, decision-support module 210a-210n may generate educational literature related to the patient's medical condition. For example, if the patient has recently given birth to a new baby, decision-support module 210a-210n may generate materials related to care of a new-born and potential medical complications or emotional problems that the mother may incur.

Optionally, system 200 may present the clinician or patient with a summarized version of the available medical and non-medical data via user module 214a-214n. Such medical and non-medical data provided to the clinician and the patient may include warnings or alerts with respect to recommended treatments or potential medical conditions of the patient. By summarizing the decision-support patient data, the clinician is not bombarded with a large quantity of information through which he or she must search. Rather, the clinician may view the current decision-supported patient data, i.e., recent laboratory test results, vital statistics, current drug usage, and the like. In this fashion, the clinician is given a simplified representation of the patient's medical condition based upon the current medical knowledge and the current patient data. Thus, medical costs are reduced and a higher quality of medical care is provided to each patient.

Generally, decision-support modules 210a-210n of system 200, either solely or in combination with medical module 216 may evaluate the stored patient data to generate decision-supported patient data for each of the patients that the clinician is to examine within a defined time period. In this manner, decision-support modules 210a-210n and system 200 assists the clinician in the treatment of the patient. The decision-support nature of the decision-supported patient data is such that suggested medical care recommendations and drug regimes are automatically generated by decision-support modules 210a-210n based upon each specific patient's needs, past and present medical conditions, family history, and various other parameters as will be discussed herein and that may be identified by one skilled in the art.

As illustrated in FIG. 2, the configuration of system 200 facilitates the delivery of patient data to the clinician in a standardized and reproducible manner. The clinician may request real-time patient data from decision-support module 210, or medical module 216 on demand and receive the patient data in a standardized format. Such patient data may be delivered to the clinician via user module 214a-214n and displayed to the clinician through a browser or other user interface. Additionally, the configuration of system 200 facilities the delivery of important or critical information and patient data to the clinician, whether in a synchronized basis or upon the occurrence of an alerted event, such as when a patient has heart attack or an adverse reaction to prescribed medication. In this manner, the clinician is quickly informed of the progress of his or her patients.

Generally, each of the modules, 210a-210n, 214a-214n, and 216 may be incorporated within various types of computer 20, remote computers 49a, 49b, and mobile information devices 55, 57 as depicted in FIG. 1. Each module 210a-210n, 214a-214n, and 216, therefore, may include system memory 22 and storage devices 50a and 50b, while optionally including hard disk drive 27, magnetic disk drive 28, optical disk drive 30, and associated interfaces 32, 33, and 34. Additionally, each module 210a-210n, 214a-214n, and 216 may communicate one with another via a variety of different manners and communication line connections. Hence, the functionality of each module 210a-210n, 214a-214n, and 216 may be incorporated within one or more of the other modules. For example, the functionality of decision-support module 210a-210n and/or of user modules 214a-214n may be incorporated within medical module 216.

Figure 3:
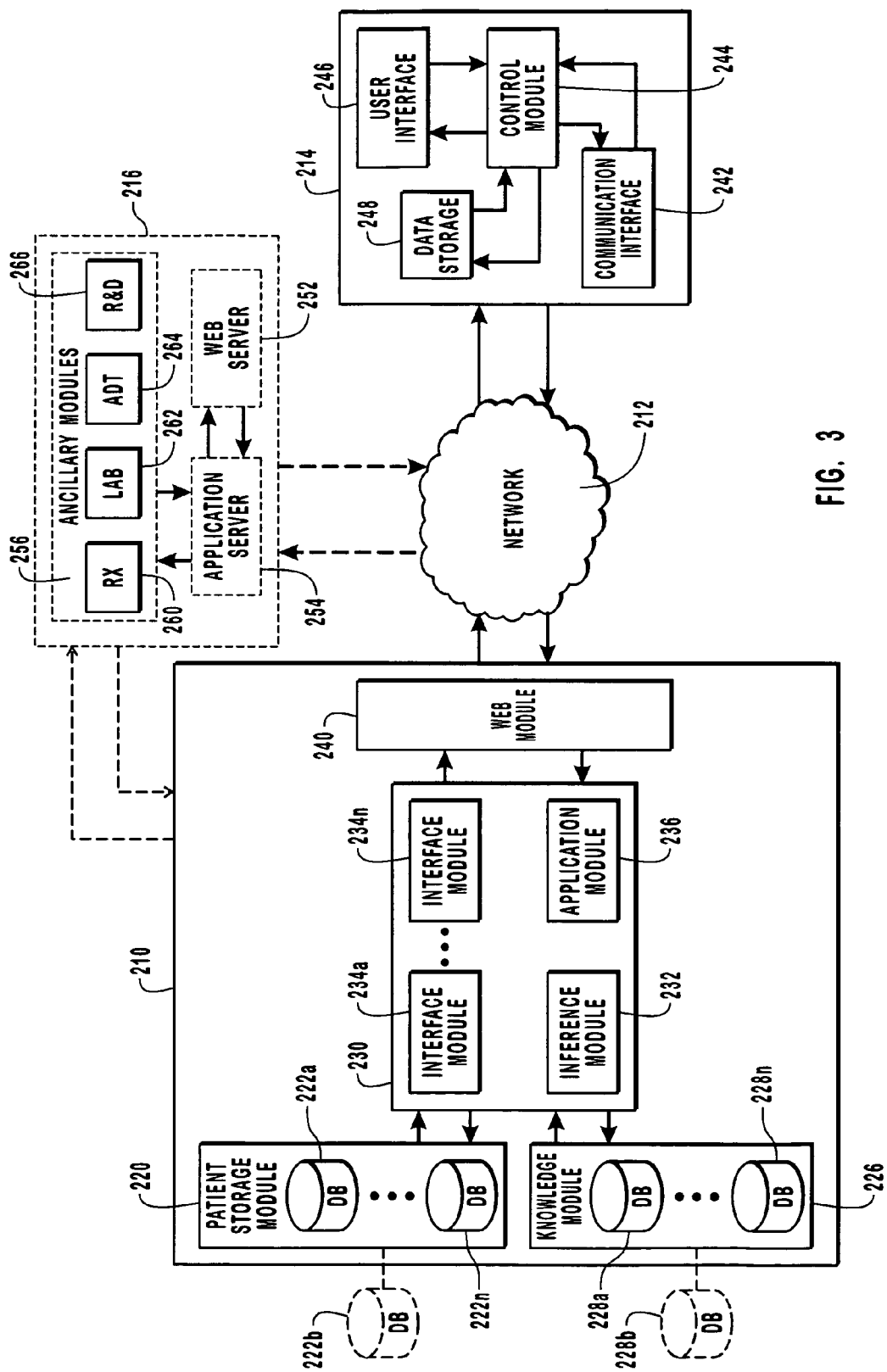
FIG. 3 is a more detailed a schematic representation of the system of FIG. 2.

With reference to the more detailed schematic representation of one embodiment of the present invention depicted in FIG. 3, only a single decision-support module 210 and a single user module 214 are depicted. The following discussion will relate to the interaction between one decision-support module 210 and one user module 214. One skilled in the art may appreciate, however, that a similar discussion may be recited for the interaction of multiple decision-support modules 210a-210n and multiple user modules 214a-214n.

According to one embodiment of the present invention, decision-support module 210 includes a patient storage module 220. Patient storage module 220 stores the patient data that may be used by the clinician in determining the medical care to be received by the patient. As illustrated, patient storage module 220 includes one or more databases 222a-222n that maintain the patient data. Each database 222a-222n may have various architectures, such as but not limited to, relational, network, flat, and hierarchical databases, with associated database management systems (not shown) that control the flow of data to and from databases 222a-222n. Although multiple databases are represented, one skilled in the art may appreciate that system 200 may include a single database.

The patient data maintained in databases 222a-222n may include, but is not limited to, the patient's billing information (e.g., name, address, telephone number, birth data, social security number, and insurance information) and patient's demographic information (e.g., age, sex, height, and weight). Additionally, databases 222a-222n include past and current: (i) medical conditions; (ii) medical care; (iii) tracked cure and failure information; (iv) medications prescribed and associated adverse effects of drug interactions; (v) laboratory tests and results; (vi) clinical consequences of treatment; (vii) family histories; (viii) genetic predispostions; (ix) decision-supported patient data and progress notes; (x) microbial susceptibilities, and the like. Such data may be stored in a variety of different fields, files, and records that are associated one with another to allow an appropriate database management system (not shown) to access the stored data in an efficient manner.

In addition to the above-recited data stored within databases 222a-222n, decision-support module 210 may store pharmacogenomic data of the patient and the patient's family to aid with the selection of medical treatment modalilties. This allows decision-support module 210 to use the patient's genetic structure to define responses to prescribed drugs and provides a more useful medical treatment recommendation. For example, a patient may be found through genetic testing to lack an enzyme necessary for a particular drug's metabolism. Hence, decision support module 210 would use such pharamacogenomic information to suggest an alternative drug that avoids toxicity and treatment failure, while being consistent with the patient's condition and pertinent medical parameters.

In accordance with another aspect of the present invention, decision-support module 210 includes a knowledge module 226. Knowledge module 226, and associated databases 228a-228n, is the repository of the medical information, data, and associated rules and parameter descriptions i.e., "knowledge", which decision-support module 210 uses to identify an unknown medical condition of a patient that is examined by the clinician. Alternatively, the "knowledge" may be used to treat a known medical condition, such as a terminal medical condition or non-curable medical condition.

The medical information and data stored within knowledge module 226 is based on information from experts within the relevant fields of medicine, such as such as Geriatric Medicine, Genetic Medicine and Gene Therapy, Cardiovascular diseases, Respiratory diseases, and the like. Therefore, knowledge module 226 includes information related to, but not limited to the following: Critical Care Medicine, Renal diseases, Genitourinary diseases, Gastrointestinal diseases, Diseases of the liver, gallbladder, and bile ducts, Hematologic diseases, Oncology, Metabolic diseases, Nutritional diseases, Endocrine diseases, Women's Health, Diseases of bone and bone mineral metabolism, Diseases of the immune system, Musculoskeletal and connective tissue diseases, Infectious diseases, HIV and Acquired immunodeficiency syndrome, Diseases of protozoa and metazoa, Neurological Diseases, Eye, Ear, Nose, and Throat diseases, Skin diseases, Pediatric Medicine, and the like.

The rules and parameter descriptions stored in knowledge module 226 may include one or more software modules, files, and records that define how decision-support module 210 uses the expert information to analyze the patient's current medical information. In this manner, the clinician is guided with the identification and treatment of a patient's medical condition. Such rules and parameters are dynamic in that as system 200 gathers more "knowledge" the rules and parameters changes to accommodate the increased knowledge. This is in contrast to many existing expert systems that utilize hard coded rules and parameters that are difficult to vary based upon an increasing knowledge base.

As with databases 222a-222n, each database 228a-228n may have various architectures, such as but not limited to, relational, network, flat, and hierarchical databases, with associated database management systems (not shown) that control the flow of data to and from databases 228a-228n.

Although FIG. 3 illustrates each database 222a-222n and 228a-228n being incorporated within decision-support module 210, one skilled in the art may appreciate that such databases 222a-222n and 228a-228n and/or patient storage module 220 and knowledge module 226 may be remotely located from decision-support module 210 Alternatively, in one configuration, patient storage module 220 and/or databases 222a-222n may be incorporated within a hospital or clinic's administrative system and/or network that allow decision-support module 210 to access the information stored therein. In another configuration, patient storage module 220 and/or databases 222a-222n are located remotely from decision-support module 210 and a hospital or clinic's administrative system and/or network.

Communicating with patient storage module 220 and/or knowledge module 226 is an intermediate module 230. Intermediate module 230 facilitates the decision-making process by providing one or more modules that interact with patient storage module 220 and/or knowledge module 226 to generate a medical condition diagnosis and medical care recommendations for the clinician. In one embodiment of the present invention, intermediate module 230 is a middle tier application server. It may be appreciated by one skilled in the art that intermediate module 230 may have various other configurations. For example, intermediate module 230 may be an application server integrally formed with medical module 216.

Intermediate module 230 includes, in one embodiment, an inference module 232. Inference module 232 controls the manner by which decision-support module 210 generates solutions to the medical condition of the patient, whether the information and data to make such solution is gathered and/or stored patient data and information contained within the knowledge module 226. Inference module 232 includes an inference engine that is commonly known by those skilled in the art. Inference module 232 communicates with patient storage module 220 and/or knowledge module 226 through a variety of different interfaces such as those developed with Enterprise Java Beans (EJB), Common Object Request Broker Architecture (COBRA), and Common Object Model (COM) compliant services. It may be appreciated that a variety of different software modules and services may be used to allow inference module 232 to communicate with patient storage module 220 and/or knowledge module 226.

Although inference module 232 is depicted as being incorporated within intermediate module 230 of decision-support module 210, one skilled in the art may appreciate that inference module 232 may be integrated into medical module 216 by connecting intermediate module 230 directly to medical module 216 by an Internet Inter-Object Request Broker Protocol (IIOP) or remotely by a Remote Method Invocation (RMI).

According to another aspect of the present invention, intermediate module 230 optionally includes interface modules 234a-234n. Interface modules 234a-234n allow intermediate module 230 and hence decision-support module 210 to communicate with medical module 216 and obtain patient data therefrom. Such communication may be via a variety of communication protocols and communication line connections. In one illustrative embodiment, interface module 234a allows communication via the Health Level 7 protocol, while interface module 234n allows communication between decision-support module 210 and medical module 216 via Extensible Markup Language (XML). It may be appreciated by one skilled in the art that various other protocols and communication line connections may allow communication between decision-support module 210 and medical module 216.

Intermediate module 230 further includes an application module 236. Application module 236 represents the various application programs that may be used by intermediate module 230 to facilitate the decision-making process to diagnose a medical treatment and provide guidance as to recommended medical procedures or treatments. For example, application module 236 may includes software to drive the decision-support process and more specifically to drive the decision made by inference module 232. In another configuration, application module 236 includes a progress note module that manipulates the decision-supported patient data into a decision-supported progress note that represents the a qualitative and quantitative analysis of the patient assessment process performed by the decision-support module 210 and the clinician and the recommended plan of medical care suggested by decision-support module 210. Such qualitative and quantitative analysis may extend over a long period, such as with an outpatient situation, or over a shorter period, such as with an inpatient situation.

To allow intermediate module 230 to transceive information to and from user module 214, one embodiment of the present invention optionally includes a web module 240. Web module 240 may be a web server that facilitates data transceiving between decision-support module 210 and user module 214. Web module 240 may transceive information and data via Hypertext Transfer Protocol (HTTP), File Transfer Protocol (FTP), Wireless Application Protocol (WAP), or various other communication protocols and communication line connections. For example, web module 240 may use TCP/IP communication protocol, a connection orientated or connectionless network protocol, via asynchronous transfer mode (ATM) technology, X.25 protocol, Frame Relay protocol, packet switching protocols, circuit switching protocols dynamic packet switching protocols, 802.11RF protocol, home network protocols, and the like to transceive data through network 212. Therefore, web server 240 and hence decision-support module 210 may use a variety of different interface types, such as but not limited to a wireless interface thereby utilizing IR, RF, satellite, blue tooth transmission and associated protocols, a modem, cable modem, ADSL connection, ISDN, Ethernet, or similar other connections, and the like.

One skilled in the art may appreciate that inclusion of web module 240 within decision-support module 210 is optional. In the event that decision-support module 210 is partially or completely incorporated within medical module 216, decision-support module 210 is devoid of web module 240 and may utilize a web module incorporated within medical module 216 to allow communication with user module 214 via network 212.

Referring again to FIG. 3, communicating with decision-support module 212 is user module 214. User module 214 is preferably a personal digital assistant (PDA) or other hand-held hardware device, including, but not limited to, a Palm Pilot, or CE based palm computer, with associated software applications and operating systems. Therefore, user module 214 may be a computer 20 and/or remote computer 49a and 49b that allows a clinician and/or patient to gather and view medical information and associated medical diagnosis and treatments.

User module 214, in one embodiment, includes a communication interface 242, a control module 244, and a user interface 246. Communication interface 242 may transceive data between decision-support module 210, medical module 216, and user module 214. Communication interface 242, therefore, may transcribe data, compress and decompress data, encrypt and decrypt data, and the like. Alternatively, the above-described operations may be performed by a combination of communication interface 242 and control module 244.

Depending on the type of communication line connection between user module 214 and network 212, and hence decision-support module 212 and optionally medical module 216, communication interface 242 may have a variety of configurations. One skilled in the art may identify various other types of communication interface that are applicable in light of the teaching contained herein. For example, communication interface 242 may be a wireless interface thereby utilizing IR, RF, satellite, blue tooth transmission and associated protocols, a modem, cable modem, ADSL connection, ISDN, Ethernet, or similar other connections, and the like.

As implied above, communication interface 242 communicates with control module 244. Control module 244 performs a number of operations and functions to allow a clinician and/or patient to gather patient data through user interface 246 and view proposed diagnosis and recommended treatments or medical procedures by way of user interface 246, such as the decision-supported patient data. Control module 244, therefore, manages the flow of data: (i) to and from the clinician and/or patient; (ii) from data storage module 248 to user interface 246; (iii) between user module 214 and decision-support module 210; and (iv) optionally from medical module 216 to user module 214.

In addition to controlling the flow of patient data between the various modules and components of system 200, control module 244 may control the configuration of user interface 246. Stated another way, control module 244, in one embodiment, may receive display instructions from the clinician regard how the decision-supported patient data and decision-supported progress note received from decision-support module 210 are to be displayed or arranged. Alternatively, control module 244 may either receive the decision-supported patient data (or the decision-supported progress note) and convert the data into a form consistent with the clinician's instructions or function with intermediate module 230 and web module 240 to generate the desired display.

In the later case, control module 244 may: (i) receive through communication interface 242 the decision-supported patient data or the decision-supported progress note; (ii) store the decision-supported patient data or the decision-supported progress note in data storage module 248, decision-support module 210, and/or medical module 216; (iii) summarize the decision-supported patient data (or decision-supported progress note) in accordance with the clinician's instructions to display the pertinent information to the clinician; and (iv) display the summarized decision-supported patient data (or decision-supported progress note) to the clinician through user interface 246.

Generally, the summarized decision-supported patient data contains the pertinent information related to the current medical status of the patient. For example, if the patient has diabetes the medical information received from decision-support module 210 will be directed to the pertinent medical conditions associated with the patient's diabetes and control module 244 will summarize the decision-supported patient data to recite the most recently acquired pulse rate, blood pressure, blood sugar level, critical warnings and alerts, and the like. Alternatively, when a therapeutic regimen is suggested, the summarized decision-supported patient data includes drug name and type, dose, route, interval and duration of therapy, critical alerts and warnings specific to the patient and the drug, patient demographics, and the like.

In this manner, control module 244 provides the clinician with the pertinent patient specific decision-supported patient data in a summarized arrangement requested by the clinician. By summarizing the pertinent data, a clinician is more capable of treating a patient in an efficient manner; with a reduction in the time required to perform normal clinician activities.

According to another aspect of the present invention, control module 244 may manage the flow of information gathered by a clinician and input into system 200 through user interface 246. Control module 244, therefore, may receive changes to current medical treatments and store the same in preparation for delivery to decision-support module 210.

For example, a clinician performing "rounds" within a hospital may employ user module 214 to track changes to medical treatment or proscribed medications made by the clinician. Control module 244 causes such changes made to the medical treatments and/or medications proscribed to be stored in data storage module 248. Such changes will be subsequently transmitted to decision-support module 210 and medical module 216 upon synchronizing of user module 214, such as hotsyncing user module 214 with decision-support module 210 and/or medical module 216 through physically inserting user module 214, such as in the form of a PDA, within a cradle or alternatively synchronizing the stored information by way of a wireless connection, satellite connection, IR connection, or such other connection known by one skilled in the art in light of the teaching contained herein.

Control module 244 may include various hardware and/or software modules to perform the above-referenced functions, such as but not limited to one or more micro-controllers, central processing units, state machines, programmable logic arrays, network logical arrays, or gates, ASIC processors, software-based controllers, combination logic, combinations thereof, and a variety of other controllers known by one skilled in the art. Control module 244 may communicate with communication interface 242, user interface 246, and data storage module 248 by a variety of connections, such as but not limited to electrical communication, an analog or digital, wireless, optical, or various other types of connection by way of one of a variety of communication line connections known by one skilled in the art.

As referenced above, a clinician may update medical information through user interface 246 and receive a graphical representation of all or a summarized version of the available medical conditions, diagnosis, and treatments of a patient through the same user interface 246. User interface 246 may also allow a clinician and/or patient to define the display configuration of the decision-supported patient data and other patient data that is transmitted to user module 214 from decision-support module 210 and/or medical module 216. A clinician may, in one embodiment, select from a number of stored display configurations, use the default display configuration, or generate a clinician specific display configuration. No matter the particular display configuration selected by the clinician, the particular display configuration assists a clinician in diagnosing, treating, and providing medical care to the patient.

In one embodiment, user interface 246 is preferably a graphical user interface (GUI), such as a web browser. One skilled in that art may identify various other interfaces that are capable of performing the desired function of allowing a clinician and/or patient to gather and subsequently view medical information. For example, user interface 246 may be a textual, interactive, drop-down menu, voice activated, and the like interface. User interface 246 may allow a user to select choices through pushing buttons, selecting icons, scanning bar codes, vocalization of procedure codes or medical treatments, or through some other method, system, hardware device, and/or software application known to one skilled in the art.

Generally, user interface 246 and communication interface 242 may be developed from a variety of software packages such as HTML, dynamic HTML (DHTML) (including JavaScript, Cascading Style Sheets, Common Gateway Interface (CGI) scripts, cookies, Java, ActiveX, Server-Side Includes (SSI)), and the like.

According to another aspect of the present invention, decision-support module 210 and user module 214 may communicate with medical module 216 via network 212. Medical module 216, as referenced above, may include various hardware and/or software modules and components associated with a medical facility, such as a hospital or clinic, a government agency, such as the Centers for Disease Control and Prevention (CDC), or some other facility that may obtain a benefit of the present invention.

As depicted in FIG. 3, medical module 216 optionally includes a web server 252 that communicates with network 212. Web server 252 provides content representative of information stored in medical module 216 over network 212 to those hardware and/or software modules that access web server 252. Upon receiving a request from a hardware and/or software modules, such as user module 214 and decision-support module 210, web server 252 provides the requested documents or information in an appropriate language, such as Hyper Text Markup Language (HTML), XML, or some other language. Web server 252 may provide the requested information via Secured Socket Layers (SSL) protocol, a Virtual Private Network (VPN), asymmetric or symmetric encryption, or some other security protocol or process known to one skilled in the art. One skilled in the art may also recognize that although a single server is depicted as part of medical module 216, medical module 216 may include a plurality of web servers 252.

Communicating with web server 252 is an application server 254. Application server 254 provides the conduit between the information stored in medical module 216 and any requests for such information through web server 252. Application server 254 acts as an intermediary between the information or data storage and the hardware and/or software modules that request access to the desired information. Application server 254 controls access to such information. In the illustrated configuration of FIG. 3, information from the ancillary module 256 passes through application server 254 upon a request through web server 252 to access the medical information stored in the ancillary module 256. Application server 254 may, optionally in combination with web server 252, authenticate access rights to the requested information.

In an alternate configuration of the present invention, when decision-support module 210 is partially or completely integrated within medical module 216, inference module 232 of decision-support module 210 may be integrated into medical module 216 by connecting intermediate module 230 directly to application server 254 of medical module 216 by an Internet Inter-Object Request Broker Protocol (IIOP) or remotely by a Remote Method Invocation (RMI).

According to another aspect of the present invention, medical module 216 includes ancillary modules 256. Ancillary modules 256 includes one or more other modules that represent various hardware and/or software modules of the individual departments within the medical facility, such as the hospital or clinic, and there associated connection to medical module 216 and network 212. As illustrated, ancillary modules 256 may include a pharmacy module 260, laboratory module 262, administration module 264, radiology 266 and the like.

Pharmacy module 260 maintains information and data representative of drugs requested and proscribed for each of a plurality of patients, whether a patient is an inpatient or an outpatient. Laboratory module 262 maintains information and data representative of the laboratory tests ordered and performed for each of a plurality of patients. Administration module 264 maintains information and data representative of the billing information and scheduling information associated with each of a plurality of patients. Radiology module 266 maintains information and data representative of the Computed Tomographic (CT) scans, fetal ultrasounds, magnetic resonance imaging (MRI), mammographs, and X-rays, ordered and performed for each of a plurality of patients.

One skilled in the art may identify various other modules that may be included within ancillary modules 256. For example, ancillary modules 256 may include computer physician entry systems, other order entry systems, and the like.

Figure 4:
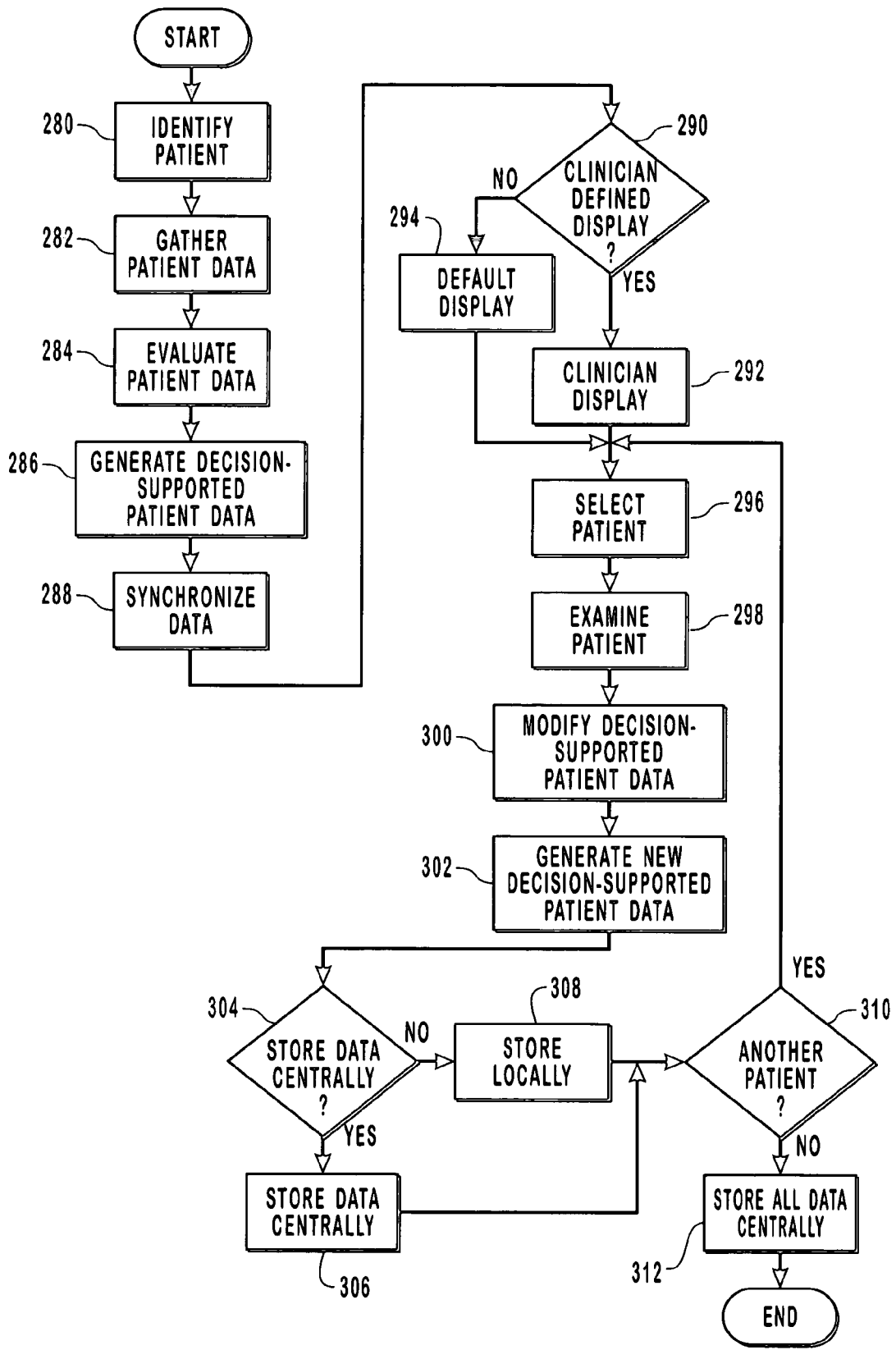
FIG. 4 is a flow diagram illustrating the flow of data in the system of FIGS. 2 and 3.

FIG. 4 is a flow diagram representing the operational process of one embodiment of the present invention. FIG. 4 depicts the processes and methodology for transceiving data in an inpatient setting between decision-support module 210 and/or medical module 216 and user module 214, such as when a clinician is performing "rounds" within a hospital or other clinical facility. It may be appreciated, that the method steps described herein are only illustrative of one method of performing the desired function.

Referring now to FIG. 4, a description of the methodology of the present invention shall be provided as it relates to obtaining decision-supported data by a clinician in an inpatient setting. The methodology description makes reference to FIGS. 2 and 3, thereby illustrating the method of processing data through the various illustrative modules and components of the present invention.

Before a clinician begins "rounds", the clinician identifies each patient with whom he or she will visit or examine, as represented by block 280. During this process the clinician may synchronize or connect user module 214 with decision-support module 210 and/or medical module 216 (FIGS. 2 and 3). This may be achieve through various communication line connections, such as but not limited to wireless, IR communication, placing user module 214 within a cradle, and the like. In this manner, a clinician may identify those patients that decision-support is required.

Upon selecting the patients to be visited or examined, decision-support module 210, either solely or in combination with medical module 216, gathers patient data for each patient selected by the clinician, as represented by block 282. This may entail each or a combination of the following: (i) searching patient module 220, with its associated databases 222*a*-222*n* (FIG. 3); (ii) searching one or more modules of ancillary module 256 (FIG. 3) of medical module 216; and (iii) receiving patient data from the clinician through user module 214.

Once decision-support module 210 gathers the patient data, inference module 232 of decision-support module 210 analyzes the patient data with the data stored within knowledge module 226, as represented by block 284. This process may involve many iterations to determine possible medical conditions, causes of medical conditions, potential treatments, such as surgery, administration of a therapeutic drug, lifestyle change, or the like, to define a recommended course of action. This may also entail verifying authorization with an insurance carrier for particular recommend treatment. In the event that an insurance carrier does not accept or will not pay for a recommended treatment, decision-support module 210 reevaluates the decision-support process to determine alternate courses of action for the particular patient.

Upon reaching a recommendation, whether a single recommendation or a ranked list of recommendations, decision-support module 210 generates decision-supported patient data specific for each patient on the list of patient's that the clinician is to visit or examine, as represented by block 286. The decision-support patient data, generally, includes all pertinent patient data that relate to the recommended treatments suggested by decision-support module 210. For example, when a therapeutic regimen is suggested, the decision-supported patient data includes drug name and type, dose, route, interval and duration of therapy, critical alerts and warnings specific to the patient and the drug, patient demographics, and the like. Such information will be specific to each patient. For example, the dose of the therapeutic drug may be defined by decision-support module 210 based upon the height, weight, age, gender, and past medical history of the patient. Although the analysis performed by decision-support module 210 may not be illustrated or displayed to the clinician, such information may be provided to the clinician via user module 214 if requested by the clinician.

While the clinician remains connected to decision-support module 210, such as when user module 214 is located within a cradle, or upon maintaining synchronization or synchronizing or connecting of user module 214 with decision-support module 210 prior to "rounds", decision-support module 210 delivers the decision-supported patient data to user module 214 such that the patient data stored therein is updated, as represented by block 288.

As data is transferred to user module 214, decision-support module 210 identifies whether a clinician has set display parameters for user interface 246 of user module 214, as represented by decision block 290. For example, the clinician may vary the manner by which user interface 246 displays the decision-supported patient data, thereby allowing a clinician to organize patient data in a format that assists the clinician in providing medical care to the patient. If the clinician has set display parameters, decision-support module 210 in cooperation with user module 214 organizes the decision-supported patient data in accordance with the clinicians selections, as represented by block 292. Alternatively, if the clinician has not set display parameters, decision-support module 210 in cooperation with user module 214 organizes the decision-supported patient data in accordance with the default display configuration, as represented by block 294.

It may be appreciated by one skilled in the art that decision-support module 210 may only deliver decision-supported patient data to user module 214 without assisting with the selection of display configuration. User module 214 alone may review whether the clinician has defined a clinician specific display configuration.

Upon receiving the required patient data (e.g., decision-supported patient data, patient data, and other patient specific information) user module 214 is ready for use by the clinician during the clinician's examination of the patients. The clinician may commence his or her "rounds" by selecting the first patient with whom he or she will visit, as represented by block 296. This may be achieved in a variety of manners depending on the particular type of user interface. For example, a clinician may select a patient from a drop-down menu, through a voice activated interface, pushing buttons, selecting icon representations of each patient, or by one of a variety of other manners known by one skilled in the art in light of the teaching contained herein.

Once the patient is selected, the clinician may perform his or her examination of the patient, as represented by block 298. The examination may be a physical examination, a question and answer session, or a combination thereof. Following the examination, the clinician may update the information stored within user module 214, as represented by block 300. Subsequently, the clinician maintains a connection or connects to decision-support module 210 and/or medical module 216, either through a cradle located at the patient's bed into which user module 214 is located or through a wireless connection, to generate new decision-supported patient data with associated recommendations and treatments, as represented by block 302. Following receipt of the new decision-supported patient data the clinician selects the desired medical treatment or regime.

Alternatively, instead of the clinician asking a number of questions as prompted by the clinician's knowledge and information contained within the decision-supported patient data, a patient may answer a number of questions posed through another user module located at the patient's bed. In this manner, when the clinician examines the patient the clinician merely has to select the desired medical treatment or regime, without connecting to decision-support module 210 to obtain new decision-supported patient data. Hence, steps related to connecting to decision-support module 210 to obtain new decision-supported patient data are optional to the flow diagram depicted in FIG. 4.

Once the desired medical treatment or regime is selected, a clinician may store the new decision-supported patient data centrally within decision-support module 210 and/or medical module 216, thereby updating the patient data stored therein, as represented by decision block 304. If the clinician wishes to store this patient's data, user module 214 connects or synchronizes with decision-support module 210 and/or medical module 216, either physically or through wireless or other remote connection, and updates the information or data stored therein, as represented by block 306. In the event the clinician does not wish to store the new decision-supported patient data centrally, user module 214 stores the new decision-supported patient data within data storage 248, as represented by block 308.

Whether the new decision-supported patient data is stored centrally or locally, the clinician may select other patients with whom he or she is to visit, as represented by decision block 310. If the answer is in the affirmative, the clinician is asked to select a new patient, as represented by block 296. Subsequently, the clinician follows the same data flow as represented by blocks 298 through 308. If the answer is in the negative, user module 214 automatically or through user prompts connects or synchronizes with decision-support module 210 and/or medical module 216, either physically or through wireless or other remote connection, to update the information or data stored therein, as represented by block 312. Such connection and/or synchronization may cause decision-support module 210 and/or medical module 216 to request functionality of ancillary module 256. For example, in the event that the medical care recommended by the clinician requires laboratory tests, user module 214 connects to laboratory module 262 to schedule such tests and notifies the nurse or other clinician assistant to obtain the necessary blood or other substances to perform the desired tests. Similarly, if a prescription medication is required, user module 214 connects with pharmacy module 260 to obtain the medication.

In this manner a clinician is able to receive decision-supported patient data that provides the clinician with recommendations as to potential medical conditions that each patient with whom he or she may have and/or provide the clinician with updated current patient data for those patients that the clinician is continually treating. By providing such decision-supported patient data, the clinician is continually educated with current medical knowledge from the extensive expert system incorporated within decision-support module 210 and/or medical module 216. This allows the clinician to provide medical care at the cutting edge of the medical knowledge and the clinician is more capable of giving each patient a high quality of medical care in an efficient manner.

According to another aspect of the present invention, user module 214 may be continuously, substantially continuously, periodically, or sporadically connected or synchronized with decision-support module 210 and/or medical module 216. User module 214 may then receive alert signals or messages from decision-support module 210 and medical module 216 related to the patient's visited by the clinician. For example, the clinician may receive an e-mail message on his or her mobile information device or user module 214 identifying an emergency with his or her patient. Alternatively, the user module 214 may receive a reminder to visit a particular patient at a particular time or request information from decision-support module 210 and/or medical module 216 on demand. In this manner, the clinician is quickly informed of the progress of his or her patients.

The present invention may be embodied in other specific forms without departing from its spirit or essential characteristics. For example, embodiments of the present invention are also disclosed in copending United States patent application entitled "Systems and Methods for Manipulating Medical Data Via a Decision Support System", filed Sep. 21, 2000, which is incorporated herein in its entirety by reference. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. In a medical decision-support system, a method for delivering decision-supported patient data from a decision-support module to a mobile user module in a controlled and repeatable manner, the method comprising the steps of:
 (a) upon identifying at least one patient which a clinician will treat during a time period and for which the clinician is to receive decision-supported patient data to assist the clinician in the medical care of the at least one patient, accessing patient data for the at least one patient from a patient storage module;
 (b) accessing updateable rules and parameters corresponding to one or more medical conditions and which are usable at the decision-support module for diagnosing medical conditions of the at least one patient, the accessed updateable rules and parameters being accessed from a medical knowledge module to assist in at least identifying the one or more medical conditions in the at least one patient;

(c) generating decision-supported patient data for the at least one patient by evaluating, at the decision-support module remote from the mobile user module, the accessed patient data and any newly collected patient data for the at least one patient delivered to the patient storage using said updateable rules and parameters, the decision-supported patient data including one or more potential medical conditions for the at least one patient and one or more recommendations for medical care for the at least one patient; and (d) transferring the generated decision-supported patient data to the mobile user module, the clinician being presented with the generated decision-supported patient data for the at least one patient which the clinician will treat in the time period in a configuration to assist the clinician in treating the at least one patient, the configuration of the generated decision-supported patient data being selected from a default configuration associated with the mobile user module or a customized configuration selected by the clinician.

2. A method as recited in claim 1, wherein the step of transferring the generated decision-supported patient data to the mobile user module comprises transferring the generated decision-supported patient data to store the relevant patient data for the at least one patient within the mobile user module.

3. A method as recited in claim 1, wherein the step of transferring the generated decision-supported patient data to the mobile user module comprises transferring the generated decision-supported patient data to present the decision-supported patient data in at least one of real-time and perceived real-time.

4. A method as recited in claim 1, wherein the medical knowledge module comprises at least one database containing expert medical rules and parameters for diagnosing medical conditions.

5. A method as recited in claim 1, wherein the generating decision-supported patient data step comprises the steps of:
(a) identifying a patient that the clinician is to examine;
(b) searching the accessed patient data for patient data corresponding to the patient; and
(c) applying the accessed updateable rules and parameters to the patient data corresponding to the patient to assist the clinician in determining if the patient has any of the corresponding one or more medical conditions.

6. A method as recited in claim 5, wherein the step of searching comprises the steps of:
(a) searching a decision-support module; and
(b) searching a medical module.

7. A method as recited in claim 1, wherein the generating decision-supported patient data step comprises evaluating the accessed patient data against an insurance carrier, a plurality of database modules, a medical module, a third-party module, or a user module.

8. A method as recited in claim 1, wherein the step for accessing updateable rules and parameters comprises the step of accessing rules and parameters used to automatically generate one of a computerized medical condition diagnosis and computerized medical care recommendation.

9. A method as recited in claim 1, wherein the accessing patient data step comprises the step of accessing patient data previously received from the mobile user module.

10. A computer-readable medium having computer-executable instructions for performing the steps recited in claim 1.

11. The method as recited in claim 1, wherein the accessed updateable rules are configured to be updated when more recent medical knowledge corresponding to the one or more medical conditions becomes available.

12. In a medical decision-support system, a computer program product for implementing a method for transceiving data between a decision-support module and a mobile user module, the computer program product comprising:
at least one computer readable medium carrying computer-executable instructions for implementing the method, wherein the computer-executable instructions comprise:
program code means for, upon identifying at least one patient which a clinician will treat during a time period and for which the clinician is to receive decision-supported patient data to assist the clinician in the medical care of the at least one patient, accessing patient data from a patient storage module;
program code means for accessing updateable rules and parameters corresponding to one or more medical conditions and which are usable at the decision-support module for diagnosing medical conditions of the at least one patient, the accessed updateable rules and parameters being accessed from a medical knowledge module to assist in at least identifying the one or more medical conditions in the at least one patient;
program code means for generating decision-supported patient data for the at least one patient by evaluating, at the decision-support module remote from the mobile user module, the accessed patient data and any newly collected patient data for the at least one patient delivered to the patient storage module using said updateable rules and parameters, the decision-supported patient data including one or more potential medical conditions for the at least one patient and one or more recommendations for medical care for the at least one patient, the decision-supported patient data capable of being transferred to the mobile user module; and
program code means for transferring the generated decision-supported patient data to the mobile user module, the clinician being presented with generated decision-supported patient data for the at least one patient which the clinician will treat in the time period in a configuration to assist the clinician in treating the at least one patient, the configuration of the generated decision-supported patient data being selected from a default configuration associated with the mobile user module or a customized configuration selected by the clinician.

13. A computer program product as recited in claim 12, further comprising program code means for storing patient data relevant to the at least one patient the clinician is to examine within the mobile user module.

14. A computer program product as recited in claim 12, wherein the knowledge base comprises at least one database containing expert medical rules and parameters for diagnosing medical conditions.

15. A computer program product as recited in claim 12, wherein the program code means for generating decision-supported patient data comprises:
(a) program code means for identifying a patient the clinician is to examine;
(b) program code means for searching the accessed patient data for patient data corresponding to the patient; and (c) program code means for applying the accessed updateable rules and parameters to the patient data corresponding to the patient to assist the clinician in determining if the patient has any of the corresponding one or more medical conditions.

16. A computer program product as recited in claim 15, wherein the program code means for searching comprises:
   (a) program code means for searching a decision-support module; and
   (b) program code means for searching a medical module.

17. A computer program product as recited in claim 12, wherein the program code means for generating decision-supported patient data comprises program code means for evaluating the accessed patient data against modules selected from the group consisting of (i) an insurance carrier, (ii) a plurality of database modules, (iii) a medical module, (iv) a third-party module, and (v) a user module.

18. A computer program product as recited in claim 12, wherein program code means for accessing updateable rules and parameters comprises program code means for accessing rules and parameters used to automatically generate one of a computerized medical condition diagnosis and a computerized medical care recommendation.

19. A computer program product as recited in claim 18, wherein the program code means for accessing patient data comprises program code means for accessing patient data the was previously received from the mobile user module.

20. The method as recited in claim 12, wherein the accessed updateable rules are configured to be updated when more recent medical knowledge corresponding to the one or more medical conditions becomes available.

21. A medical decision-support system, comprising:
   (a) a decision-support module configured to:
      (i) access patient data for at least one patient from a patient storage module to assist in the medical care of the at least one patient;
      (ii) access updateable rules and parameters corresponding to one or more medical conditions, the accessed updateable rules and parameters being accessed to assist in at least identifying the one or more medical conditions in the at least one patient;
      (iii) generate decision-supported patient data for the at least one patient by evaluating the accessed patient data and newly collected patient data for the at least one patient delivered to the patient storage module using said updateable rules and parameters, the decision-supported patient data including at least one of (i) one or more potential medical conditions for the at least one patient and (ii) one or more recommendations for medical care for the at least one patient; and
      (iv) transfer the generated decision-supported patient data to a mobile user module, the clinician being presented with decision-supported patient data for the at least one patient in a configuration to assist the clinician in treating the at least one patient; and
   (b) a user module remotely located from the decision-support module and configured to receive the generated decision-supported patient data from the decision-support module, the mobile user module comprising a user interface configured to present the generated decision-supported patient data in a configuration to assist the clinician in treating the at least one patient, the configuration of the generated decision-supported patient data being selected from a default configuration associated with the mobile user module or a customized configuration selected by the clinician.

22. A medical decision-support system as recited in claim 21, wherein the medical knowledge module comprises a plurality of databases.

23. A medical decision-support system as recited in claim 21, wherein the decision-support module communicates with the medical knowledge module to generate the decision-supported patient data.

24. A medical decision-support system as recited in claim 21, wherein the decision-support module comprises a plurality of ancillary modules.

25. A medical decision-support system as recited in claim 21, wherein the medical knowledge module is updateable as more recent medical knowledge corresponding to the one or more medical conditions becomes available.

26. A medical decision-support system as recited in claim 21, wherein decision-support module receives patient data from the user module.

27. A medical decision-support system as recited in claim 21 wherein the user module communicates with the decision-support module by way of a communication protocol selected from the group consisting of (i) a connection orientated protocol and (ii) a connectionless network protocol.

28. A medical decision-support system as recited in claim 21, wherein the user module comprises a mobile user module configured to communicate in real-time with the decision-support module.

29. A medical decision-support system as recited in claim 21, wherein the decision-support module communicates with the user module via a network.

30. A medical decision-support system as recited in claim 29, wherein the network is selected from a group consisting of (i) a local area network, (ii) a wide area network, (iii) a wireless network, (iv) a packetized network, and (v) a real-time network.

31. A medical decision-support system as recited in claim 21, wherein the decision-support module communicates with a medical knowledge module to generate the decision-supported patient data.

32. A medical decision-support system as recited in claim 31, wherein the medical knowledge module comprises a plurality of ancillary modules.

33. The system as recited in claim 21, wherein the user interface comprises one or more of a graphical user interface, an interactive user interface, a voice recognition user interface, and a textual user interface.

* * * * *